US010646331B2

(12) United States Patent
Hirsch et al.

(10) Patent No.: US 10,646,331 B2
(45) Date of Patent: May 12, 2020

(54) OSSICULAR PROSTHESIS AND METHOD AND SYSTEM FOR MANUFACTURING SAME

(71) Applicant: University of Maryland, Baltimore, Baltimore, MD (US)

(72) Inventors: Jeffrey Hirsch, Lutherville, MD (US); David J. Eisenman, Silver Spring, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 196 days.

(21) Appl. No.: 15/963,332

(22) Filed: Apr. 26, 2018

(65) Prior Publication Data
US 2018/0311035 A1    Nov. 1, 2018

Related U.S. Application Data

(60) Provisional application No. 62/490,276, filed on Apr. 26, 2017.

(51) Int. Cl.
| *A61F 2/18* | (2006.01) |
| *A61B 34/10* | (2016.01) |
| *G05B 19/4099* | (2006.01) |
| *B33Y 80/00* | (2015.01) |

(52) U.S. Cl.
CPC .............. *A61F 2/18* (2013.01); *A61B 34/10* (2016.02); *B33Y 80/00* (2014.12); *G05B 19/4099* (2013.01); *A61B 2034/102* (2016.02); *A61B 2034/105* (2016.02); *A61B 2034/108* (2016.02); *A61F 2002/183* (2013.01); *A61F 2240/002* (2013.01); *A61F 2240/004* (2013.01); *G05B 2219/49023* (2013.01)

(58) Field of Classification Search
None
See application file for complete search history.

(56) References Cited

U.S. PATENT DOCUMENTS

| 6,354,299 | B1 * | 3/2002 | Fischell | A61N 1/36025 |
| | | | | 128/899 |
| 7,668,325 | B2 * | 2/2010 | Puria | H04R 25/606 |
| | | | | 381/322 |
| 2004/0039244 | A1 * | 2/2004 | Kroll | H04R 25/606 |
| | | | | 600/25 |
| 2011/0046731 | A1 * | 2/2011 | Wiens | A61F 2/18 |
| | | | | 623/10 |
| 2012/0065730 | A1 * | 3/2012 | Edwards | A61B 17/29 |
| | | | | 623/10 |
| 2014/0303728 | A1 * | 10/2014 | Steinhardt | A61F 2/18 |
| | | | | 623/10 |
| 2017/0360578 | A1 * | 12/2017 | Shin | G09B 23/286 |
| 2018/0042718 | A1 * | 2/2018 | Remenschneider | A61F 2/18 |
| 2019/0201189 | A1 * | 7/2019 | Steinhardt | A61F 2/18 |

* cited by examiner

*Primary Examiner* — Ramesh B Patel
(74) *Attorney, Agent, or Firm* — Whiteford, Taylor & Preston, LLP; Gregory M. Stone

(57) ABSTRACT

Disclosed herein is a customized ossicular prosthesis suitable for treatment of conductive hearing loss due to ossicular chain defects, and a method and system for manufacturing the same. Medical imaging equipment can detect specifically designated landmarks in normal human middle ear ossicles, including significant anatomic differences in those structures. Those anatomic features are used to generate a customized ossicular prosthesis specifically configured for a particular patient's anatomy using 3D printing techniques and devices.

15 Claims, 19 Drawing Sheets

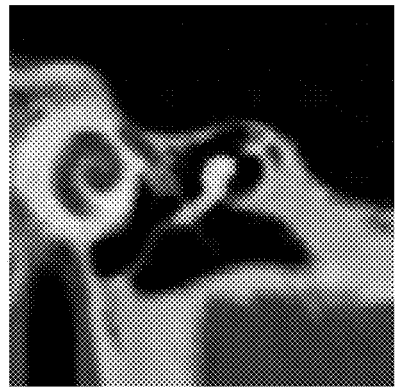
FIG. 3(a)
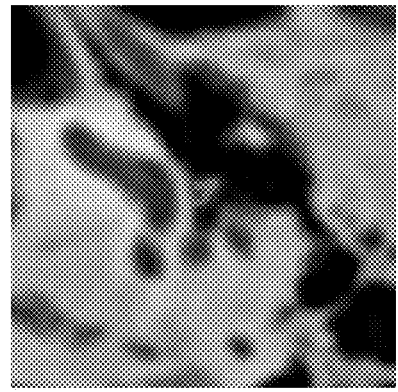
FIG. 3(b)
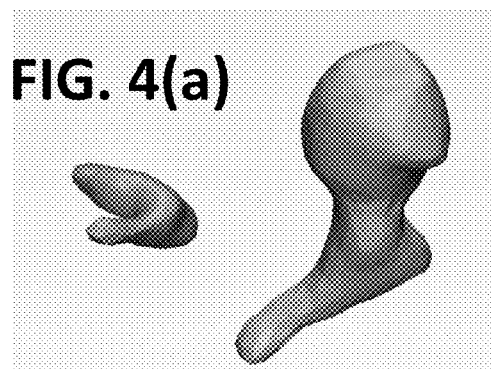
FIG. 4(a)
FIG. 4(b)

OSSICULAR PROSTHESIS AND METHOD AND SYSTEM FOR MANUFACTURING SAME

CROSS REFERENCE TO RELATED APPLICATION

This application claims the benefit of U.S. Provisional Application No. 62/490,276 titled "Ossicular Prosthesis and Method of Manufacturing," filed Apr. 26, 2017 by the inventors herein, which application is incorporated herein by reference in its entirety.

FIELD OF THE INVENTION

The present invention relates generally to individually customized prostheses, and more particularly to the creation of a customized ossicular prosthesis using medical imaging to model those portions of a patient's middle ear anatomy that are amenable to imaging, and generating a customized prosthesis for a particular patient's unique middle ear anatomy that engages those portions of the patient's middle ear anatomy that are amenable to imaging.

BACKGROUND

Conductive hearing loss due to ossicular abnormalities occurs commonly due to trauma, infection, cholesteatoma, surgery to treat these diseases, and congenital anomalies, amongst other causes. Surgical reconstruction of the ossicular chain is a well-established procedure for repair of ossicular defects, but is still plagued by high failure rates, with success rates in closing the air-bone gap to less than 20 dB ranging generally only from 55%-75%. Poor hearing results in many cases can be attributed to anatomical factors and persistence or recurrence of an underlying disease process, such as tympanic membrane retraction, middle ear atelectasis, fibrosis or mucosal pathology. However, none of these fully accounts for persisting air-bone gaps following ossiculoplasty. That these factors do not fully account for the failure rates is also implied by the fact that similar results are obtained with ossicular chain reconstruction following middle ear trauma, a situation in which most of those factors are not an issue. Some degree of hearing loss can be attributable to the design of current prostheses, which do not capture all of the mechanical advantages of the normal ossicular chain. Nevertheless, it is still likely that improper fit, due to both inaccurate size, angulation, and position of the prosthesis, plays a significant role. In one series with long-term follow-up, more than 40% of failures were attributed to prosthesis size or surgeon related errors. Proper intraoperative sizing of a prosthesis is challenging, and can be affected by limited exposure and variability in the anatomic relationships of the ossicular remnants to each other or to the tympanic membrane, as well as by post-operative changes during the healing process. In particular, the medial-lateral distances between ossicular remnants, the anterior-posterior offsets, and the position of and their relationship to the tympanic membrane or neo-tympanic membrane vary widely from patient to patient in the pathologic setting, and are not always readily amenable to reconstruction with off-the-shelf prostheses.

Further, persisting conductive hearing loss following ossicular chain reconstruction is multifactorial. A significant variable in many cases is likely the underlying disease process, which may render the ear unsuitable for reconstruction over the long term. Chronic infections and associated chronic Eustachian tube dysfunction can result in stiffness of the ossicular remnants, middle ear fibrosis, middle ear atelectasis, recurrent otitis media and other factors that decrease the chances of a satisfactory hearing result, either due to intrinsic limitations to adequate sound conduction, or from displacement and/or extrusion of the prosthesis. Nevertheless, technical factors such as imprecise sizing and placement of a prosthesis also play a significant role. These data are supported by the observation that outcomes are not significantly better, if at all, for reconstruction following traumatic ossicular discontinuity, a situation in which chronic infection and Eustachian tube dysfunction are not usually a factor.

3D printed solutions have been shown to be successful adjuncts to surgical techniques. Accurately reproducing a patient's specific pathologic anatomy for preoperative planning is a common thread. Patient specific custom made anatomic models used in preoperative planning have been shown to decrease operative time and in one report to also decrease intraoperative blood loss. Additionally, models allowing for accurate surgical simulation in orthopedics and cardiovascular procedures have enhanced preoperative decision-making, improved precision and increased work efficiency. Prosthesis fabrication using 3D printed techniques is another developing field.

More particularly, three-dimensional (3D) printing has been used for a wide variety of medical applications. Custom 3D printing of an individualized ossicular prosthesis would be a potential solution for the range of anatomic variation encountered in the pathological middle ear. Custom designed prostheses could decrease the rate of post-operative prosthesis displacement, and improve the hearing outcomes, by increasing the likelihood of a proper fit. Custom printed prostheses would minimize the need for intraoperative estimates of size, and would therefore also decrease surgical time, with resultant cost savings. However, current technologies have not yet proven themselves suitable for application to the small anatomic variations found in the middle ear. Specifically, the small size of the middle ear and its ossicles present challenges both for reliable image acquisition to provide accurate data for prosthesis design, and for printing of prostheses that faithfully reproduce the measured differences.

SUMMARY OF THE INVENTION

Disclosed herein is an ossicular prosthesis and method for manufacturing the same using medical imaging (e.g., CT-based imaging) of particularly selected landmarks of a patient's middle ear anatomy to generate a 3D model of portions of the patient's middle ear anatomy, which in turn are used to generate an ossicular prosthesis that is customized to a patient's specific middle ear anatomy. Such prostheses may minimize the impact of variables that have previously presented challenges in ossicular chain reconstruction, and consequently increase success rates.

In accordance with certain aspects of an embodiment of the invention, a method for generating an ossicular prosthesis that is customized to a patient's unique middle ear anatomy is disclosed, comprising the steps of: receiving at a processor image data representing an anatomy of a patient's middle ear from a medical imaging machine; converting at the processor the image data representing an anatomy of a patient's middle ear into 3D model data representing an electronic 3D model of an ossicular prosthesis that is customized to a patient's unique middle ear anatomy; generating at the processor a data input file configured to instruct a computer controlled manufacturing machine to create a physical ossicular prosthesis conforming to the 3D model; and transmitting from the processor the data input file to a computer controlled manufacturing machine to cause the computer controlled manufacturing machine to generate the physical ossicular prosthesis.

In accordance with further aspects of an embodiment of the invention, an ossicular prosthesis that is customized to a patient's unique middle ear anatomy is disclosed, which prosthesis if formed by the foregoing method.

In accordance with still further aspects of an embodiment of the invention, a system for manufacturing an ossicular prosthesis that is customized to a patient's unique middle ear anatomy is disclosed, comprising: a medical imaging machine; a computer system in data communication with the medical imaging machine; and a computer controlled manufacturing machine in data communication with the computer system; the computer system including a processor operably configured to: receive at the processor image data representing an anatomy of a patient's middle ear from the medical imaging machine; convert at the processor the image data representing an anatomy of a patient's middle ear into 3D model data representing an electronic 3D model of an ossicular prosthesis that is customized to a patient's unique middle ear anatomy; generate at the processor a data input file configured to instruct the computer controlled manufacturing machine to create a physical ossicular prosthesis conforming to the 3D model; and transmit from the processor the data input file to a computer controlled manufacturing machine to cause the computer controlled manufacturing machine to generate the physical ossicular prosthesis.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

FIG. 3 is an exemplary mask of a patient's malleus (FIG. 3(*a*)) and stapes (FIG. 3(*b*)) formed from CT imaging of the patient's middle ear.

FIG. 4 is an exemplary computer-generated 3D object representing the patient's stapes (FIG. 4(*a*)) and malleus (FIG. 4(*b*)) from the masks of FIG. 3.

FIG. 7(*b*) shows a schematic representation of data from Table 1 for patient 1 ("Pr 1") from a top view of an ossicular prosthesis in accordance with certain aspects of an embodiment of the invention.

DETAILED DESCRIPTION OF THE PREFERRED EMBODIMENTS

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
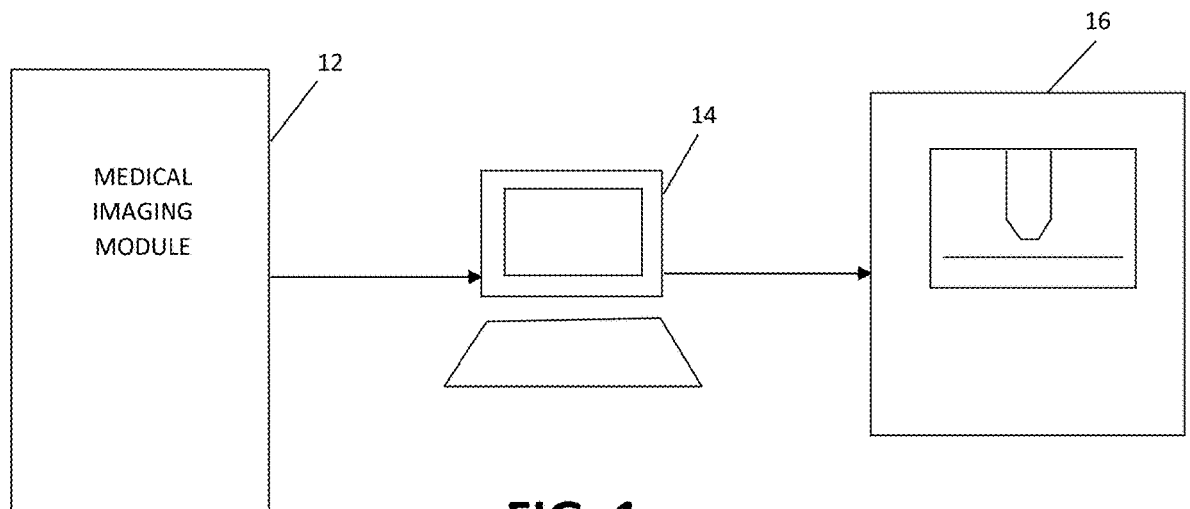
FIG. 1 shows a schematic view of a system for manufacturing an ossicular prosthesis in accordance with certain aspects of an embodiment of the invention.

FIG. 1 is a schematic view of a system 10 for manufacturing an ossicular prosthesis in accordance with certain aspects of an embodiment of the invention. System 10 includes a medical imaging machine 12, which may by way of non-limiting example comprise a computed tomography (CT) or magnetic resonance imaging (MRI) machine configured to scan and produce images of a portion of a patient's body. Medical imaging machine 12 is in data communication with computer system 14 which may comprise one or more computers having a processor, a monitor or display device, and operator interface controls all preferably of standard configuration. Computer system 14 is likewise in data communication with a computer controlled manufacturing machine 16, which may by way of non-limiting example comprise a 3D printer or a CNC milling machine, with a 3D printer being particularly preferred. Those skilled in the art will recognize that, rather than using a single computer system 14 to carry out the entire process set forth herein, multiple computers can perform separate steps of the overall process, with each respective step managed by a respective technician skilled in that particular aspect of the overall process. The data generated in one process step on one computer can then be transferred for the next process step to another computer, such as (by way of non-limiting example) via a network connection.

In use, and as further detailed below, medical imaging machine 12 is used to scan and to generate images of the middle ear anatomy of a patient. An exemplary medical imaging machine 12 may comprise a Brilliance CT 64 Channel CT machine, which is commercially available from Philips Healthcare, Amsterdam, The Netherlands. Medical imaging machine 12 may make a plurality of scans of the patient's middle ear, where each scan represents a thin slice of the patient's middle ear anatomy.

The plurality of scans generated by medical imaging machine 12 are then used by computer system 14, employing commercially available CAD (computer aided design) or CAM (computer aided manufacturing) software programs, to generate 3D models of portions of the patient's middle ear anatomy, and particularly of at least portions of the patient's malleus and stapes. An exemplary software program may comprise a Mimics Innovation Suite software application, which is commercially available from Materialise, Belgium. From the 3D models of the patient's malleus and stapes, computer system 14 generates a 3D model of an ossicular prosthesis that include elements having surfaces that are customized for that particular patient's specific middle ear anatomy. More particularly, computer system 14 generates a 3D model of an ossicular prosthesis having a linear trough that is sized to mate closely with the manubrium of the patient's malleus, a cup sized to mate closely with the capitulum (head) of the patient's stapes, and a connecting strut extending between the linear trough and the cup in an orientation with respect to one another that matches the orientation of the mating elements of that patient's middle ear anatomy.

Data describing the 3D model of the ossicular prosthesis is then transmitted to computer controlled manufacturing machine 16 for fabrication of the prosthesis. An exemplary computer controlled manufacturing machine 16 may comprise a Form2 3D printer, which is commercially available from FormLabs, Somerville, Mass. With regard to an exemplary embodiment, computer controlled manufacturing machine 16 may fabricate the ossicular prosthesis using, by way of non-limiting example, fused-deposition modeling (FDM), selective laser sintering (SLS), stereolithography (SLA), electron beam melting (EBM), or any other 3D printing or additive manufacturing process.

Figure 2:
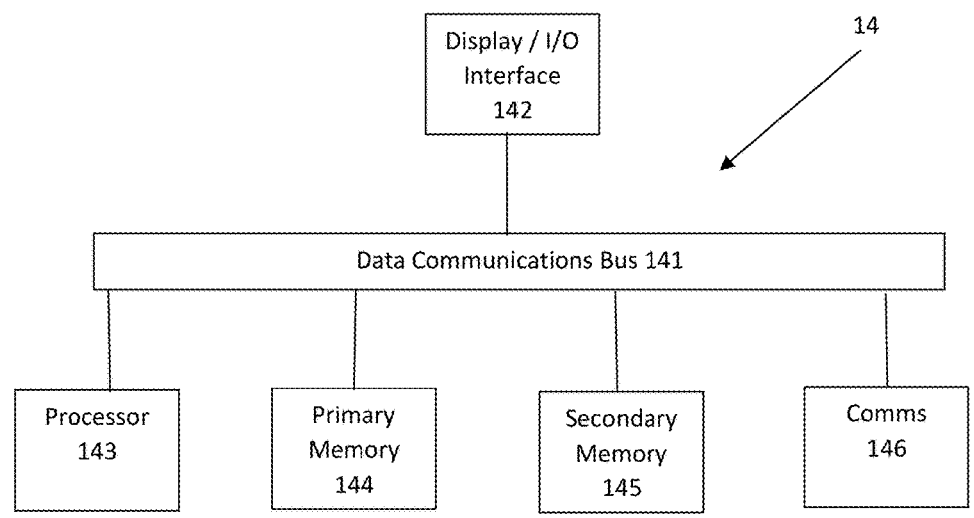
FIG. 2 shows a schematic view of an exemplary computer system for use in the system of FIG. 1.

With reference to FIG. 2, computer system 14 may, by way of non-limiting example, comprise a personal computer or other processing device including a communications bus 141, or other communications infrastructure, which communicates data to other elements of computer system 14. For example, communications bus 141 may communicate data (e.g., text, graphics, video, other data) between bus 141 and an I/O interface 142, which may include a display, a data entry device such as a keyboard, touch screen, mouse, or the like, and any other peripheral devices capable of entering and/or viewing data as may be apparent to those skilled in the art. Further, computer system 14 includes a processor 143, which may comprise a special purpose or a general purpose digital signal processor. Still further, computer system 14 includes a primary memory 144, which may include by way of non-limiting example random access memory ("RAM"), read-only memory ("ROM"), one or more mass storage devices, or any combination of tangible, non-transitory memory. Still further, computer system 14 includes a secondary memory 145, which may comprise a hard disk, a removable data storage unit, or any combination of tangible, non-transitory memory. Finally, computer system 14 may include a communications interface 146, such as a modem, a network interface (e.g., an Ethernet card or cable), a communications port, a PCMCIA slot and card, a wired or wireless communications system (such as Wi-Fi, Bluetooth, Infrared, and the like), local area networks, wide area networks, intranets, and the like.

Each of primary memory 144, secondary memory 145, communications interface 146, and combinations of the foregoing may function as a computer usable storage medium or computer readable storage medium to store and/or access computer software including computer instructions. For example, computer programs or other instructions may be loaded into the computer system 14 such as through a removable data storage device (e.g., a floppy disk, ZIP disks, magnetic tape, portable flash drive, optical disk such as a CD, DVD, or Blu-ray disk, Micro Electro Mechanical Systems ("MEMS"), cloud data storage, and the like). Thus, computer software including computer instructions may be transferred from, e.g., a removable storage or hard disc to secondary memory 145, or through data communications bus 141 to primary memory 144.

Communication interface 146 allows software, instructions and data to be transferred between the computer system 14 and external devices or external networks. Software, instructions, and/or data transferred by the communication interface 146 are typically in the form of signals that may be electronic, electromagnetic, optical or other signals capable of being sent and received by communication interface 146. Signals may be sent and received using a cable or wire, fiber optics, telephone line, cellular telephone connection, radio frequency ("RF") communication, wireless communication, or other communication channels as will occur to those of ordinary skill in the art.

Computer programs, when executed, allow processor 143 of computer system 14 to implement the methods discussed herein for manufacturing an ossicular prosthesis according to computer software including instructions.

Computer system 14 may perform any one of, or any combination of, the steps of any of the methods described herein. It is also contemplated that the methods according to the present invention may be performed automatically, or may be accomplished by some form of manual intervention.

The computer system 14 of FIG. 2 is provided only for purposes of illustration, such that the invention is not limited to this specific embodiment. Persons having ordinary skill in the art are capable of programming and implementing the instant invention using any computer system.

A system in accordance with FIG. 1 was used to confirm the feasibility of using such system to generate a customized ossicular prosthesis in accordance with the methods disclosed herein. Three formalin-fixed cadaveric human temporal bones with no macro- or microscopic evidence of pathology were chosen as cadaveric models. Working under a binocular operating microscope with conventional middle ear surgical instruments, a tympanomeatal flap was elevated and the incus was removed from each bone. The bones were labeled for identification with bicortical drill holes through the squamosa (one, two or three holes).

In the current embodiment, imaging of the cadaver temporal bones was obtained using a CT protocol on a Brilliance CT 64 Channel (Philips Healthcare, Amsterdam, The Netherlands). Imaging parameters were as follows: slice thickness 0.67 mm with 0.33 mm overlap; tube rotation time 0.75 seconds; filter set to Detail; tube voltage 140 kVp and current 300 mAs; collimation 64×0.625; matrix 768; resolution set to HI; and scan field of view 200 mm. The printer for fabrication of the prostheses was a Form2 3D printer (FormLabs, Somerville, Mass.). The printer uses stereolithographic (SLA) technology on an optically cured resin. Print parameters were a layer thickness of 25 microns using the black photoreactive resin. Digital prosthesis design was accomplished with the Mimics Innovation Suite (Materialise, Belgium).

The ossicular prosthesis is designed to reestablish ossicular continuity following removal of the incus. The basic prosthesis design comprises a trough for the manubrium of the malleus and a cup for the stapes capitulum, connected by a rigid columellar strut. For example, the design includes mimicking a typical sculpted incus interposition graft, and is generally mechanically similar to many prefabricated partial ossicular replacement prostheses (PORP's). From CT imaging of the middle ear, a mask is created of the malleus and stapes, as seen in FIGS. 3(a) and 3(b).

The malleus is a relatively large and dense bone compared to the stapes. It is well characterized by CT imaging and the creation of its mask is straightforward for persons skilled in the art using commercially available tools. In contrast, the stapes is very small and is not as radiodense as the malleus. Fortunately, the capitulum and neck are the most radiodense part of the stapes and are usually well seen on CT. The inventors herein have found that a suitable, customized ossicular prosthesis may be generated using a computer controlled manufacturing machine 16 by obtaining and using visualizations of only these portions of the patient's stapes as the contact point for the prosthesis. The crura of the stapes are more gracile-shaped and usually faintly resolved by CT imaging, if at all. From the mask of the malleus and stapes, a 3D shape is generated, as shown in FIG. 4. Once these two landmarks are characterized, the prosthesis can be designed.

Figure 5:
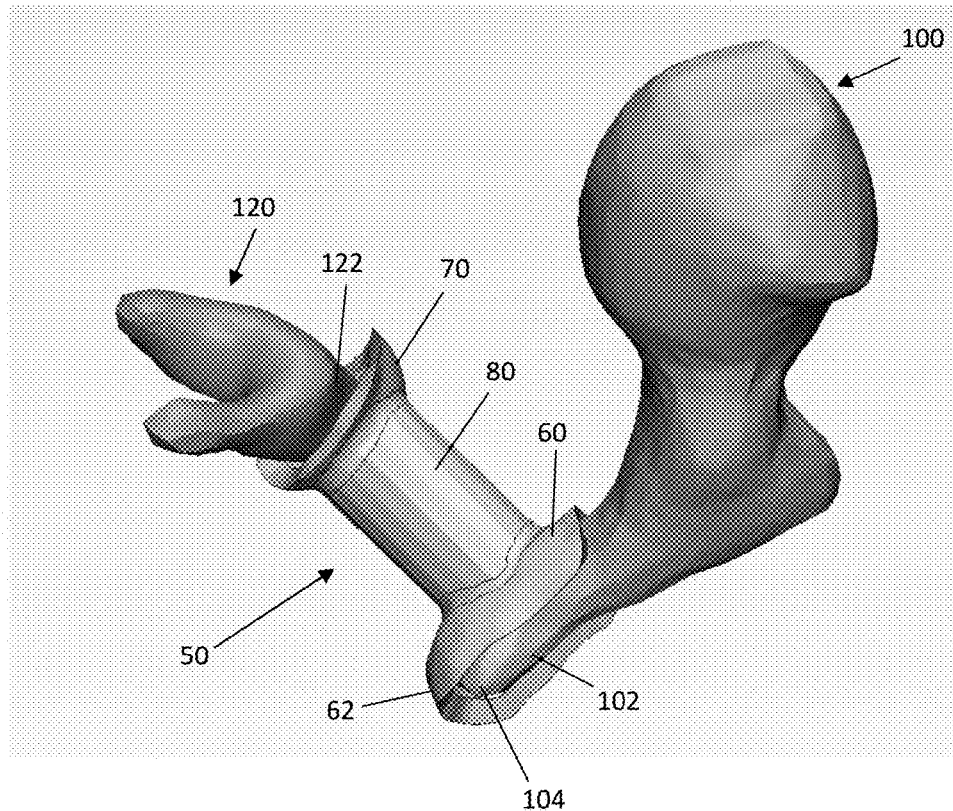
FIG. 5 is an exemplary computer-generated 3D object representing a customized ossicular prosthesis connecting the stapes and malleus of FIG. 4.

The basic design of the prosthesis 50 is a linear trough 60 and cup 70 on either end with a connecting strut 80, as shown in FIG. 5. The linear trough 60 is configured to align with and fit over the manubrium 102 of the malleus (shown generally at 100). The trough 60 has a closed, curve-shaped end 62 that fits over the distal end of the manubrium, the umbo 104. The cup 70 fits over the capitulum 122 of the patient's stapes 120. The strut 80 is a fabricated cylinder shape that connects the deep surface of the trough 60 to the superficial surface of the cup 70.

Figure 6A:
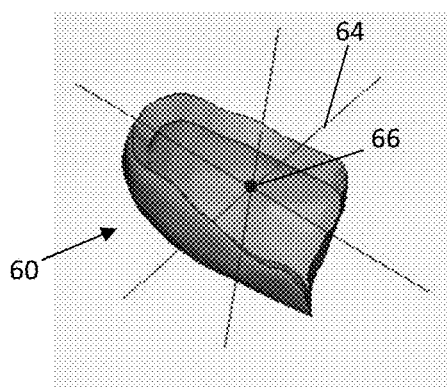
FIG. 6 depicts an inertial axis of rotation used to establish a definition of position and angle of position for both the malleus trough (FIG. 6(*a*)) and stapes cup (FIG. 6(*b*)).
Figure 6B:
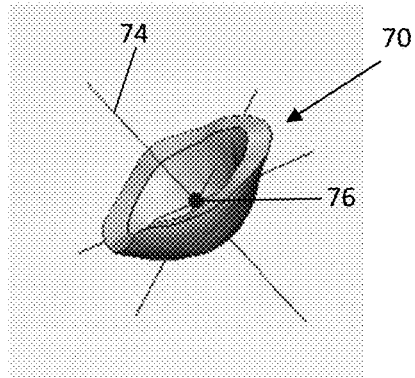

Accurately quantifying the model is important for understanding anatomic variations and establishing a format for reproducibility. The inertial axis of rotation was used to establish a definition of position and angle of position for both the malleus trough (shown in FIG. 6(a)) and stapes cup (shown in FIG. 6(b)). The primary axis 64 of the malleus trough 60, and the primary axis 74 of the cup 70, are shown in FIGS. 6(a) and 6(b), respectively, in each case comprising the line that is perpendicular to the face of the concave shape for each part.

Figure 7A:
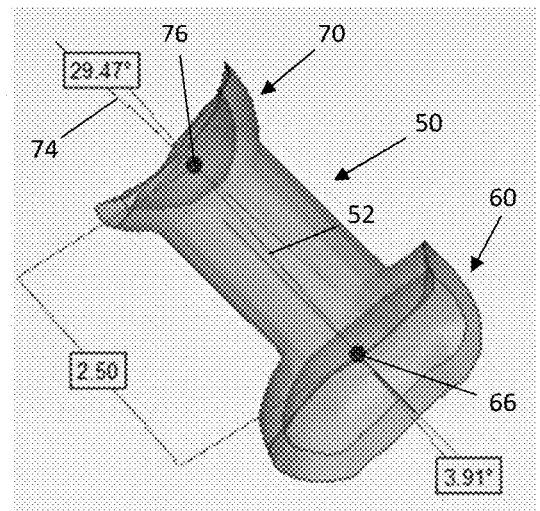
FIG. 7(*a*) shows a schematic representation of data from Table 1 for patient 1 ("Pr 1") from a side perspective view of an ossicular prosthesis in accordance with certain aspects of an embodiment of the invention.
Figure 7B:
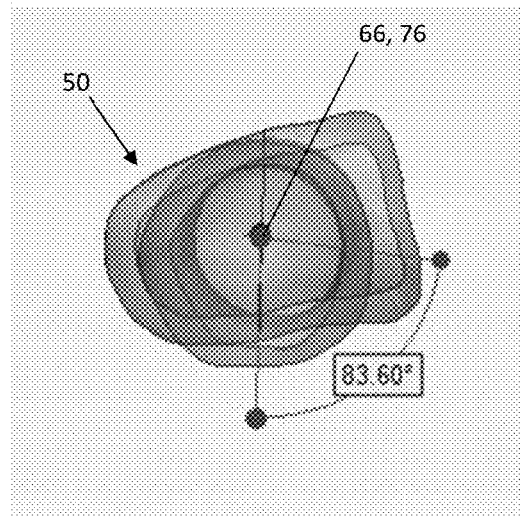

Inertial axis of rotation is a mesh-based calculation of the modeled solid shape. The center of rotation and primary axis are calculated by the modeling software based on the unique design of the shape. Table 1 below summarizes the quantifying data for the exemplary prosthesis generated for each cadaver middle ear produced during testing of the ossicular prosthesis in accordance with aspects of the invention. FIG. 7(a) shows a schematic representation of the same data from Table 1 for patient 1 ("Pr 1") from a side perspective view of the ossicular prosthesis 50 (showing rotation from centerline and prosthesis length measurements). Likewise, FIG. 7(b) shows a schematic representation of the same data from Table 1 for patient 1 ("Pr 1") from a top view of the ossicular prosthesis 50 (showing rotation from trough to cup angle).

TABLE 1

Quantification data for each prosthesis. (Pr 1—fabricated prosthesis for ear with one hole. Pr 2—fabricated prosthesis for ear with two holes. Pr 3—fabricated prosthesis for ear with three holes)

| | Cup | | | | Through | | | | Distance | |
| --- | --- | --- | --- | --- | --- | --- | --- | --- | --- | --- |
| | Center of inertia | | | Rotation from centerline | Center of inertia | | | Rotation from centerline | between centers of inertia | Rotation from cup to through |
| | X | Y | Z | (degrees) | X | Y | Z | (degrees) | (mm) | (degrees) |
| Pr 1 | −1.33 | 218.03 | 333.56 | 29.47 | −0.55 | 215.84 | 332.63 | 3.91 | 2.50 | 83.60 |
| Pr 2 | 11.92 | 221.91 | 219.00 | 37.84 | 11.63 | 220.18 | 217.85 | 10.50 | 2.09 | 30.45 |
| Pr 3 | −4.09 | 207.58 | 101.18 | 21.28 | −4.43 | 205.78 | 100.14 | 11.74 | 2.10 | 10.30 |

A line 52 extending from the center of inertia 66 defined by the malleus trough 60 to the center of inertia 76 defined by the stapes cup 70 is the prosthesis length. The same line 52 connecting the two centers of inertia is also used as a reference line to define the angular deviation or rotation from centerline of the primary axis 64 of the malleus trough 60, and from the primary axis 74 of the stapes cup 70. Then, the angular rotation from a plane defined by the trough 60 rotation from centerline angle to a plane defined by the cup 70 rotation from centerline angle (as shown in FIG. 7(*b*)) was defined as the rotation of trough to cup.

Figure 8:
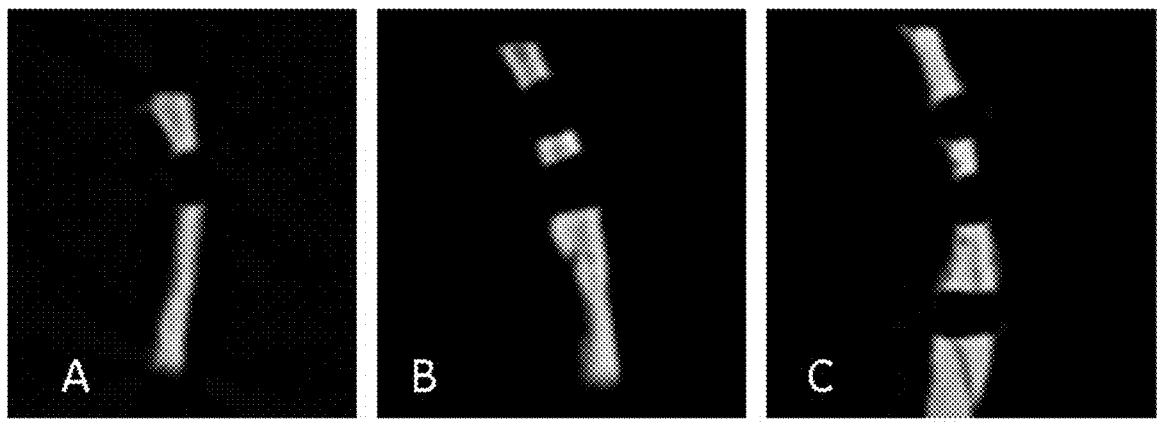
FIG. 8 shows sections of patients' calvarium with identifying bicortical holes for each temporal bone of a cadaver used in a blind study.

A blind study was conducted, in which each cadaver middle ear was marked with a set number of bicortical drill holes (1 hole, 2 holes, or 3 holes) in a portion of the calvarium, as shown in FIG. 8. This made each bone unique and easy to differentiate both visually and by CT imaging. The model ossicular prosthesis was fabricated from the CT imaging data from each cadaver middle ear. Each model was embossed with a symbol on the torus shape sinter box that cradled the prosthesis, as in the example shown in FIG. 9. While simply for purposes of distinguishing among the formed ossicular prostheses, and by way of non-limiting example, the symbols comprised an equal sign (=) for the cadaver temporal bone with one hole, a chevron (^) for the bone with two holes, and an asterisk (*) for the bone with three holes. Four surgeons, including two attending physicians with practices limited to Otology and two chief residents, both of whom had already completed senior level Otology rotations, then performed insertion of each prosthesis into each middle ear, blinded to the bone from and for which each was designed. The surgeons were asked to match each prosthesis to its correct parent bone.

The results from such blind study showed each prosthesis to be unique. The lengths of the prosthesis between the respective centers of inertia ranged from 2.09 mm to 2.50 mm. The rotation from centerline of the trough ranged from 3.91 degrees to 11.74 degrees and the rotation from centerline of the cup from 21.28 degrees to 37.84 degrees. The rotation from the trough to the cup ranged from 10.30 degrees to 83.60 degrees. Four surgeons were asked to match the three prostheses, each with a unique identifying symbol, to the temporal bone with the best fit. The surgeons completed their task on separate days, blinded to the correct match. Each of the four surgeons was able to correctly match each prosthesis to its parent temporal bone. The chances of this occurring randomly are 1:1,296.

The embodiments discussed herein show that 3D-printed ossicular replacement prostheses are unique in size and shape when using CT imaging as a basis for modeling, and that these differences are detectable by Otologic surgeons, who can accurately match the individual prostheses to their parent bones. The important landmarks within the middle ear are readily detectable during image interpretation of the middle ear. The malleus is usually well-seen and masking of that bone is straightforward. The stapes is a much smaller bone and has a much smaller mass to attenuate the CT image beam. As a result, the crura of the stapes, the thinnest part of the bone, are not well seen. However, the capitulum and neck of the stapes are more dense, and usually more reliably detected during image interpretation. This is important, because the stapes capitulum is where one side of the prosthesis rests. Once masks are made of these two landmarks, a model can be designed and fabricated. The printer used to fabricate the exemplary prosthesis described herein used SLA technology. The resolving threshold of the printer is on the order of centimicrons in the XY plane and decimicrons in the Z axis. This allows for an accurate representation of the model to be fabricated without significant intrinsic errors from the printer to be introduced to the prosthesis. The true test of accuracy, however, is if the prosthesis model fits in the space for which it was designed. In four separate trials with different surgeons, each surgeon was able to accurately match the correct prosthesis to its intended temporal bone. This further supports that the differences in size and shape for each prosthesis are meaningful and detectable by the surgeon. Additionally, such evidence shows that it is possible to fabricate a custom made middle ear prosthesis using CT imaging of the temporal bone, modeling software, and a desktop SLA printer.

Figure 9:
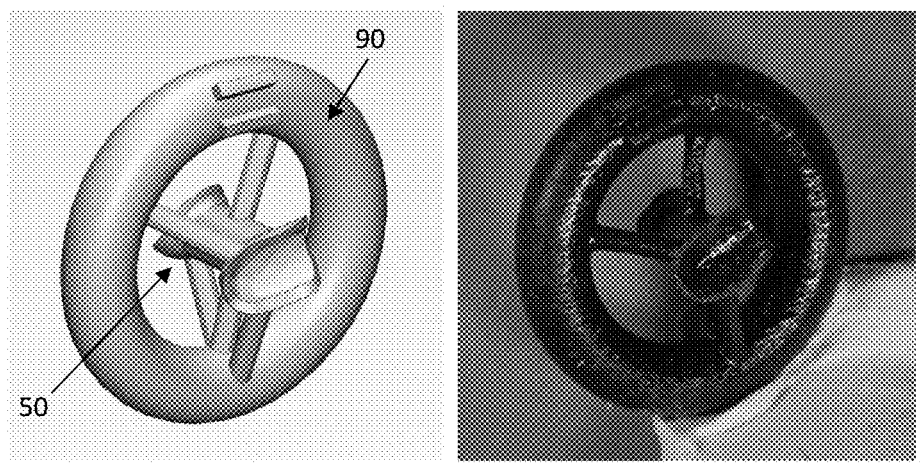
FIG. 9 shows an exemplary computer-generated 3D object representing a customized ossicular prosthesis, and a photograph of a fabricated ossicular prosthesis for ear #1 of Table 1.

As noted above, accurate quantification of the middle ear for fabrication of a custom prosthesis does present unique challenges. The process starts with identification of the important landmarks. As previously mentioned, the important landmarks for ossicular prosthesis construction are detectable with CT imaging protocols. The landmarks form the basis and starting point for fabrication of the prosthesis. As a result, subtle anatomic variation is inherently captured in the design of the prosthesis. Thus, establishing a method to accurately quantify parameters of the prosthesis also captures the subtle anatomic variation from ear to ear. Once the model was designed, then the next challenge is printing this very small part. Almost immediately apparent was the increased risk of losing the part during post processing due to its size. This was mitigated by utilizing a sinter box. The sinter box is a designed cage around a part that is fabricated with the part during the printing process. This, in essence, prints a larger part making it more difficult to lose. Additionally, it also provides a way to label the part and increases ease of handling. The torus cradle 90 as seen in FIG. 9 is the sinter box used during printing of the exemplary prosthesis 50 discussed above.

Figure 10:
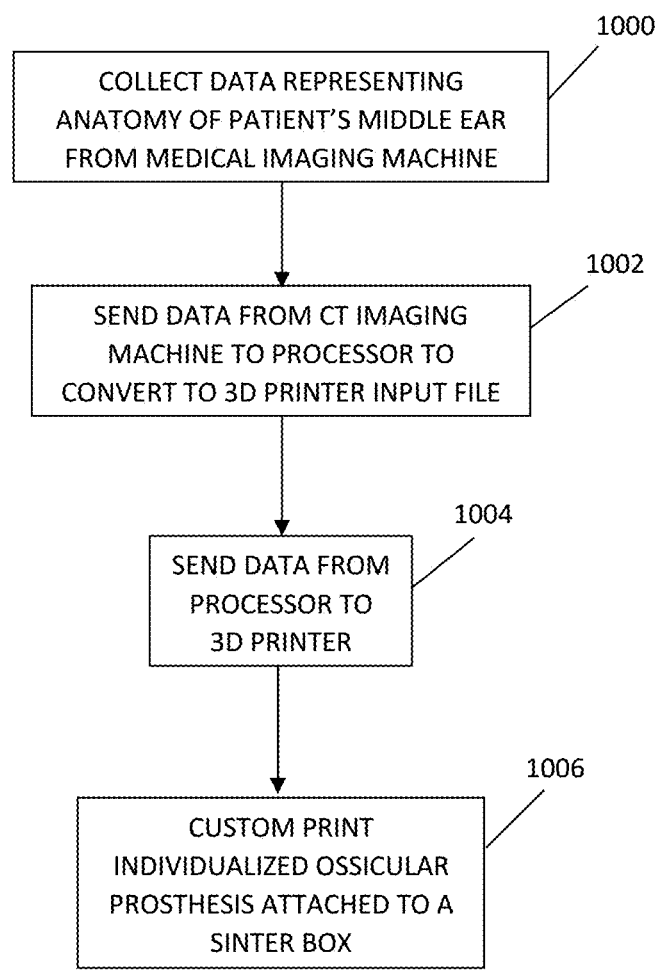
FIG. 10 is a schematic view of a method for generating an ossicular prosthesis that is customized for a specific patient's unique middle ear anatomy in accordance with certain aspects of an embodiment of the invention.

FIG. 10 provides a schematic view of a method for manufacturing an ossicular prosthesis in accordance with certain aspects of an embodiment of the invention. At step 1000, medical imaging machine 12 collects data representing the anatomy of a patient's middle ear, such as by scanning through use of CT scanning methods the patient's middle ear. As shown in FIG. 12(*a*) depicting a user interface screen presented by computer system 14 to a user, a user may designate custom window and level settings to optimize the view of the patient's stapes (window depicted in FIG. 12(*a*) is −950 and level is 3071 (max)). FIG. 12(*b*) shows a user interface screen reflecting a mask of the patient's malleus generated by medical imaging machine 12. Here, the bone mask captures the malleus margins accurately, although minor manual adjustments will be made to separate the malleus from the adjacent bone, the processes for which are well known to those skilled in the art. Likewise, FIG. 12(*c*) shows a user interface screen reflecting a mask of the patient's stapes generated by medical imaging machine 12. Here, the stapes mask will only capture the head of the stapes or the incudostapedial joint, whichever is left. The crus are to be manual added, such as through use of an "Edit Masks" tool in the 3D digital prosthesis design software discussed below, the processes for which are well known to those skilled in the art.

At step 1002, such data is sent from medical imaging machine 12 to computer system 14, so that processor 143 may, through execution of digital prosthesis design software (such as by way of non-limiting example, Mimics Innovation Suite from Materialise, Belgium), process such data to generate a computer controlled manufacturing machine input file, such as a 3D printer input file suitable for production of a customized ossicular prosthesis in accordance with aspects of the invention. Processing such data to generate a 3D printer input file is discussed in greater detail below with reference to FIG. 11. Next, at step 1004, computer system 14 sends the newly generated computer controlled manufacturing machine input file to computer controlled manufacturing machine 16, such as a 3D printer. Finally, at step 1006, computer controlled manufacturing machine 16 generates an ossicular prosthesis that is customized for a specific patient's unique middle ear anatomy, such as by custom printing the individualized ossicular prosthesis positioned within a sinter box in a 3D printer (see FIGS. 12(*r*)-12(*t*)).

Figure 11:
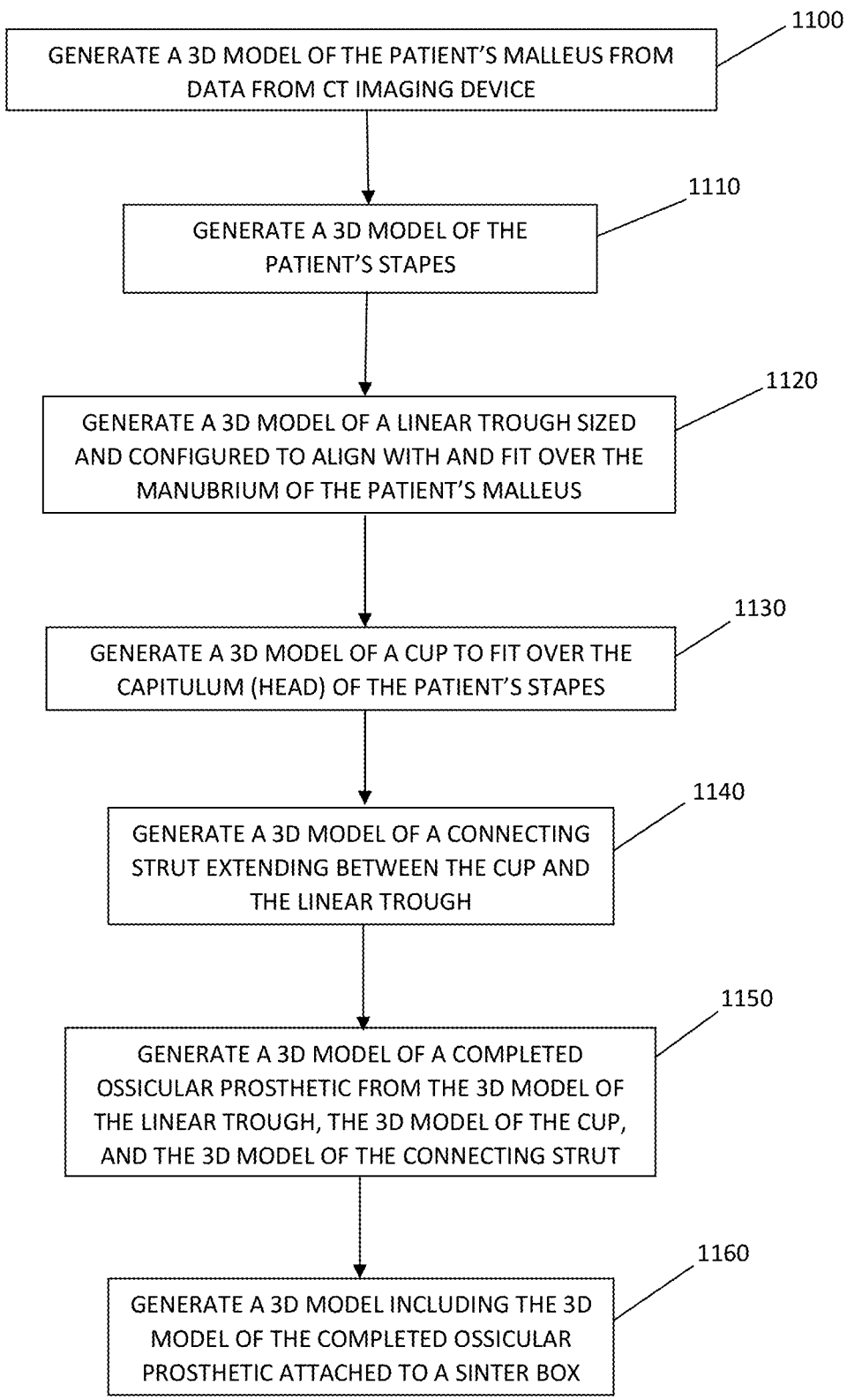
FIG. 11 is a schematic view of a method for generating a computer controlled manufacturing machine input file for use in the method of FIG. 10.
Figure 12A:
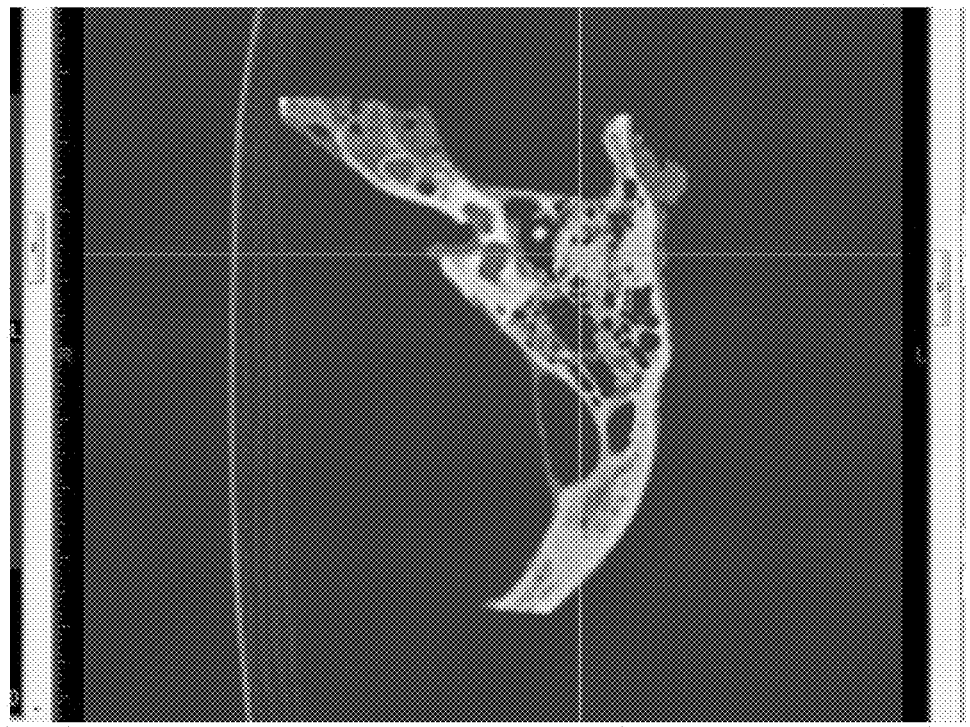
FIGS. 12(*a*)-12(*y*) show user interface screens presented by computer system 14 to a user while carrying out methods in accordance with certain aspects of an embodiment of the invention.
Figure 12B:
Figure 12C:
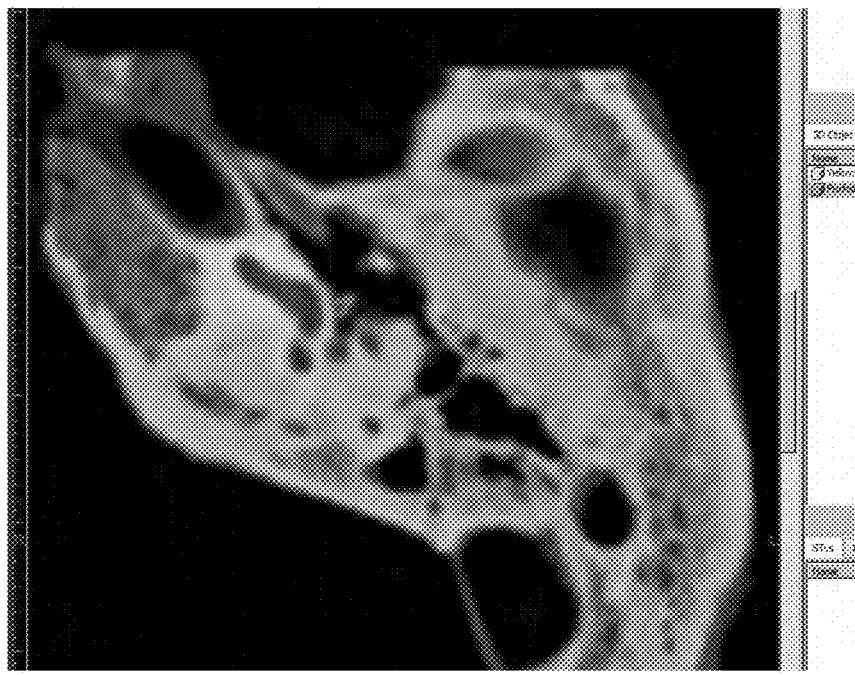
Figure 12D:
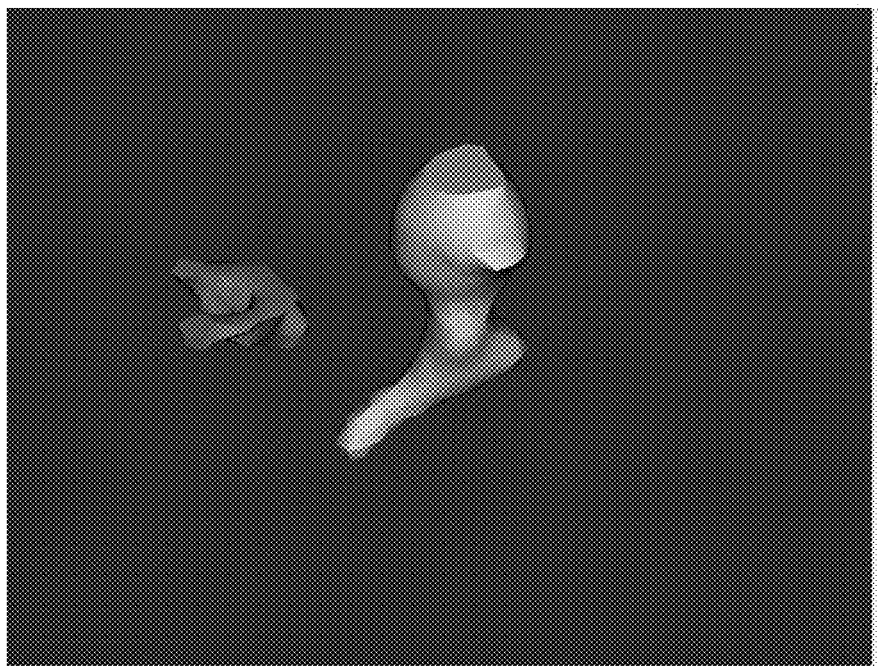
Figure 12E:
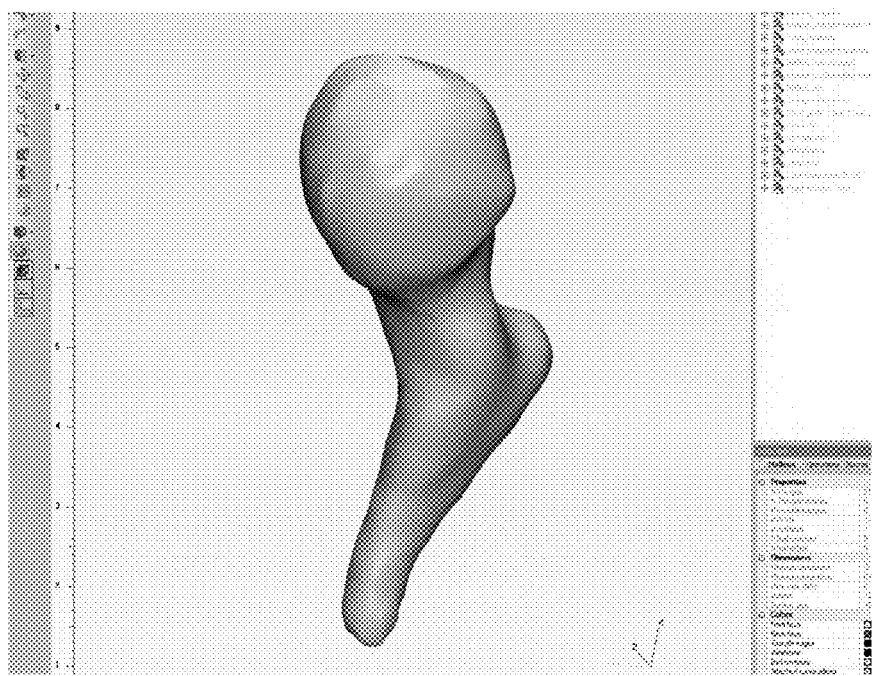
Figure 12F:
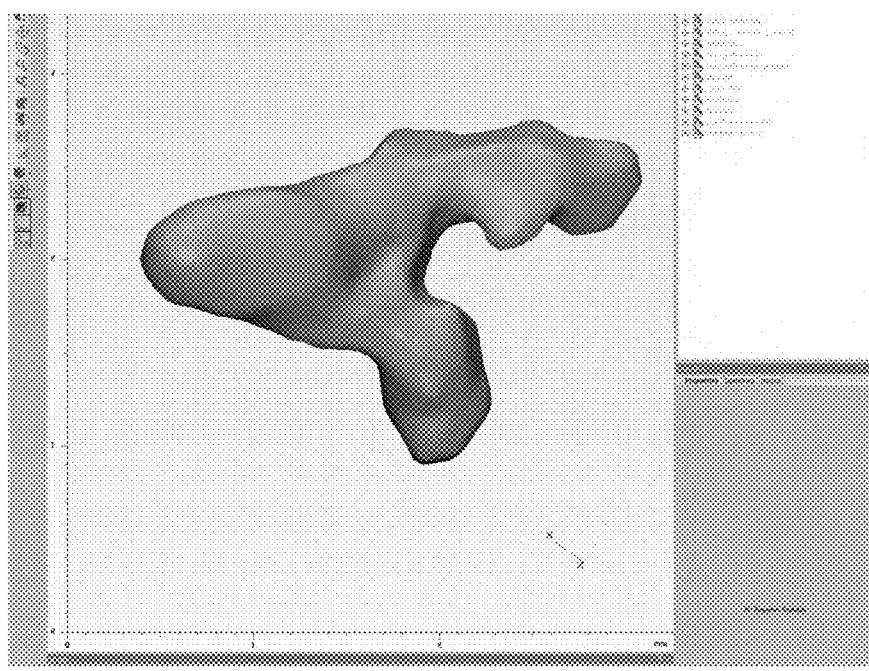
Figure 12G:
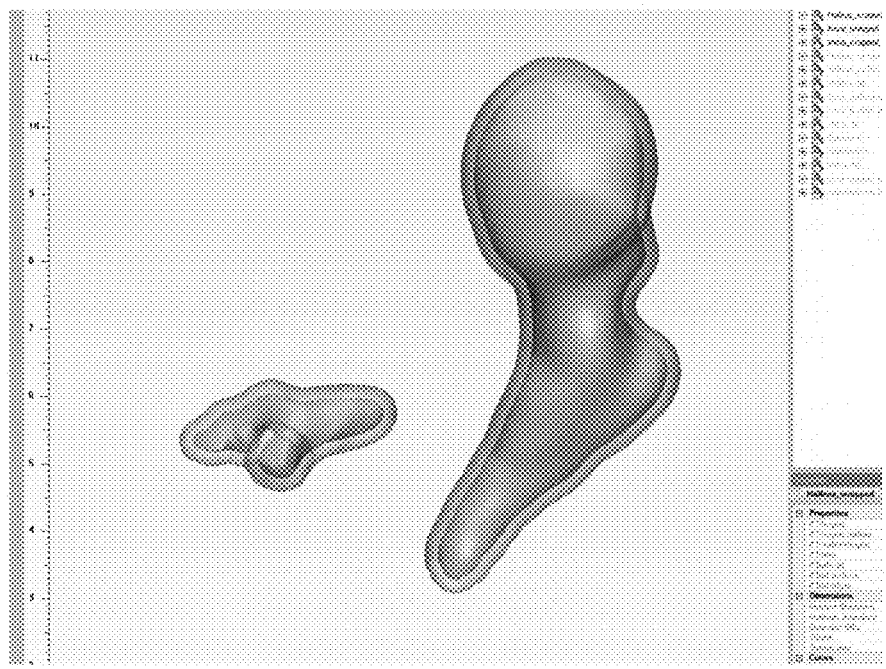
Figure 12H:
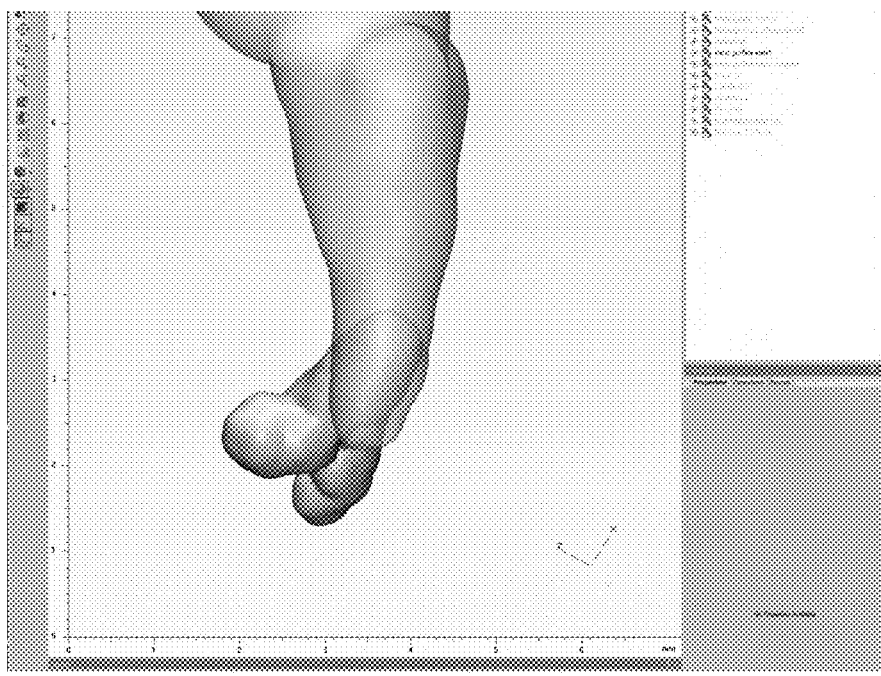
Figure 12I:
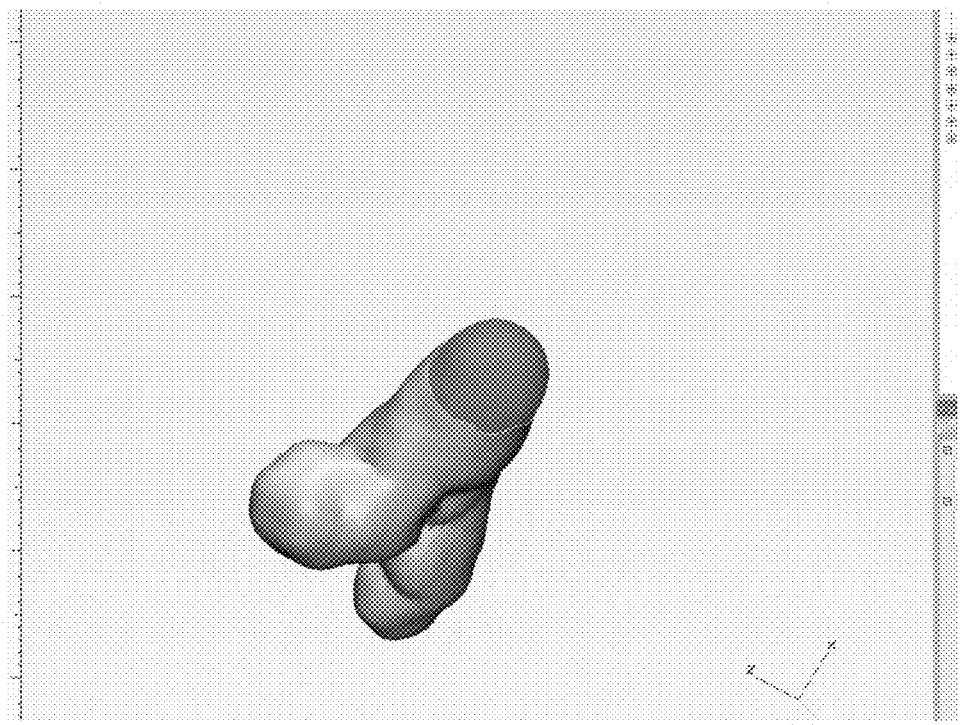
Figure 12J:
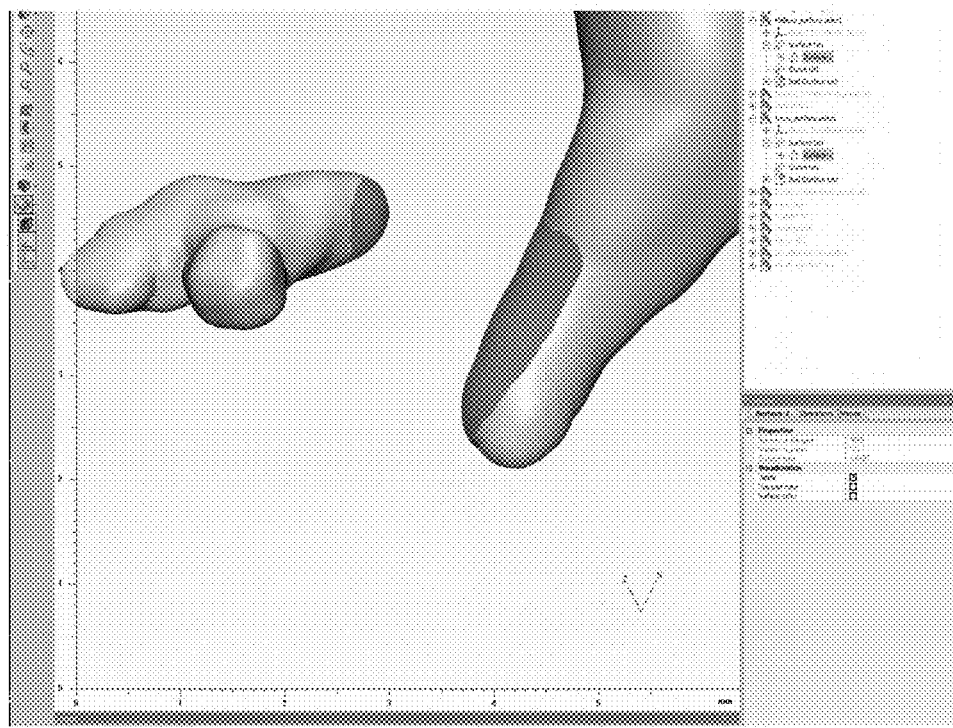
Figure 12K:
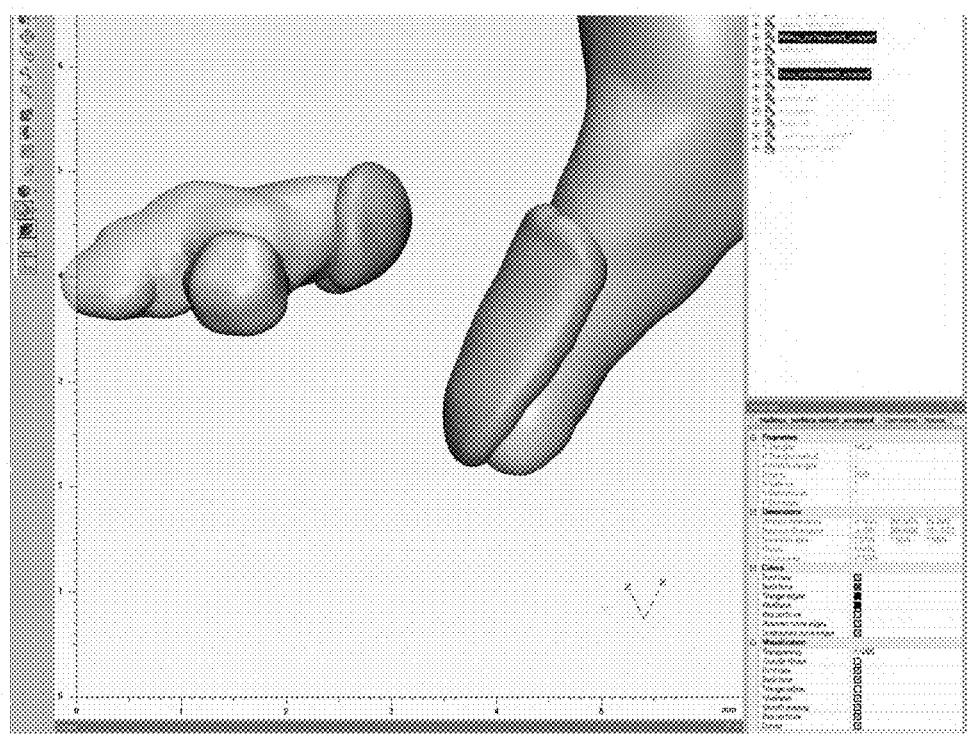
Figure 12L:
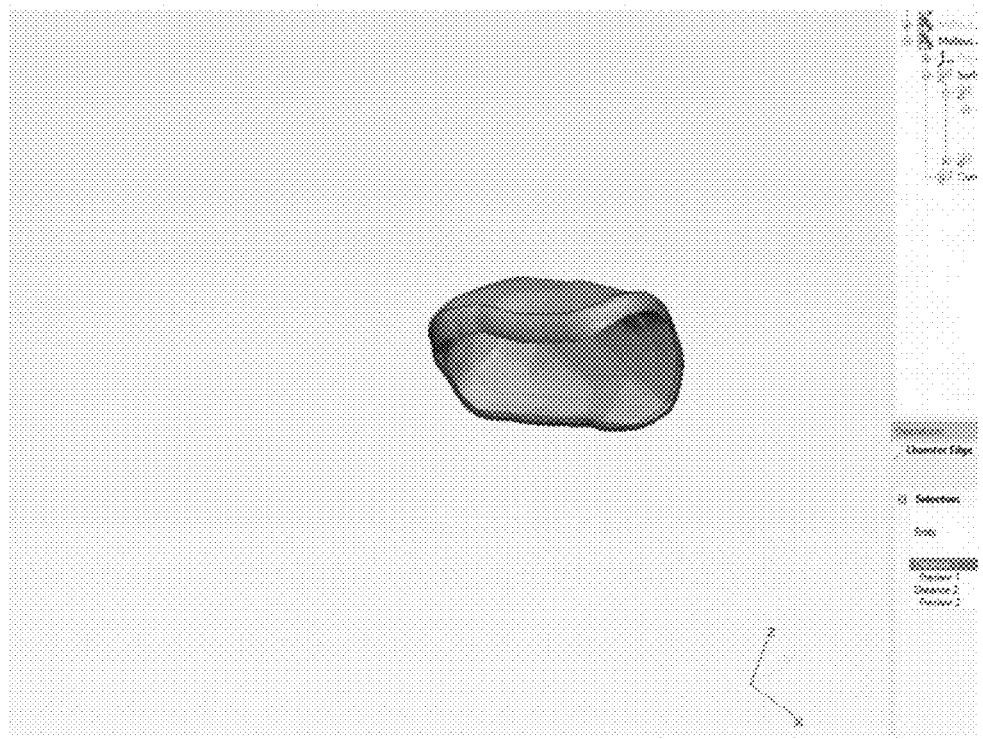
Figure 12M:
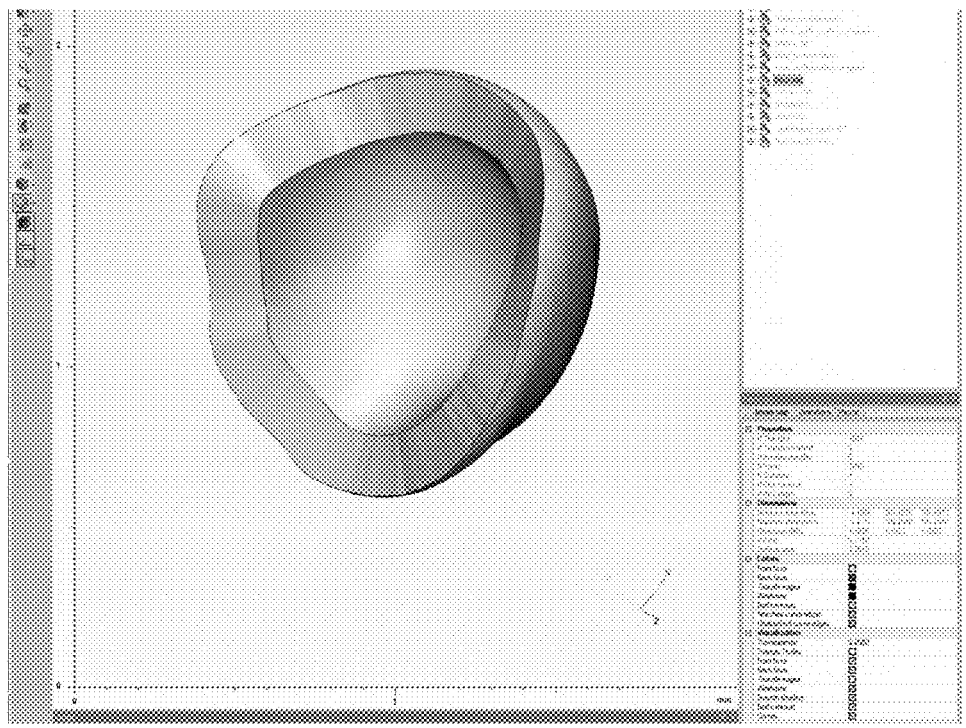
Figure 12N:
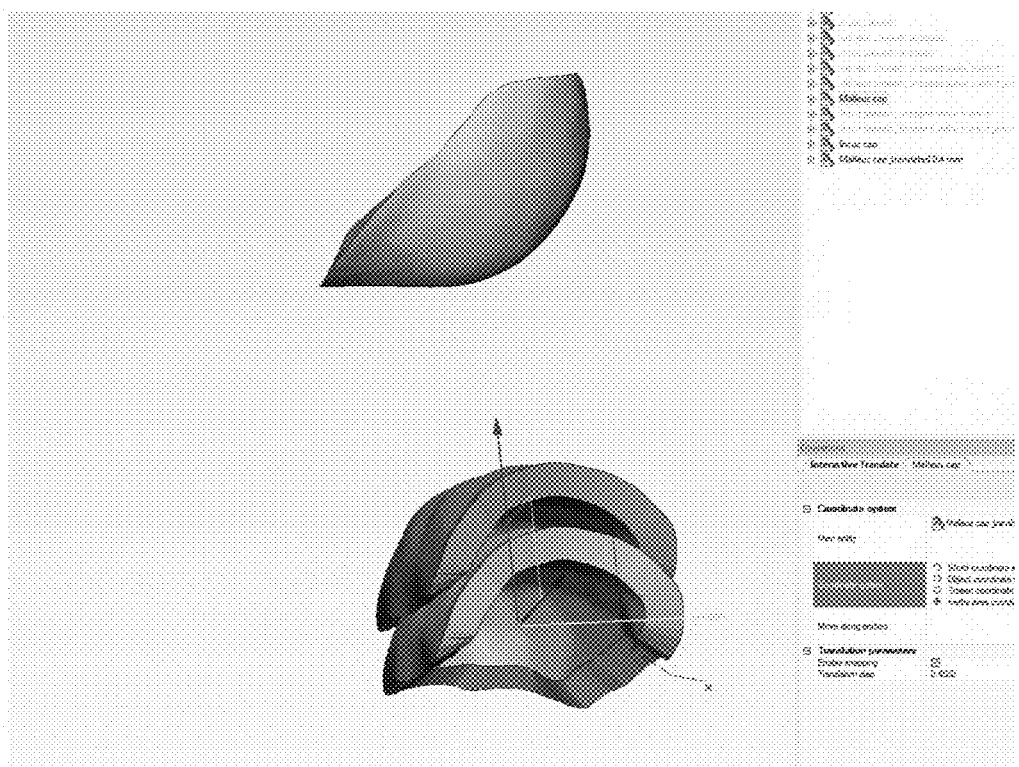
Figure 12O:
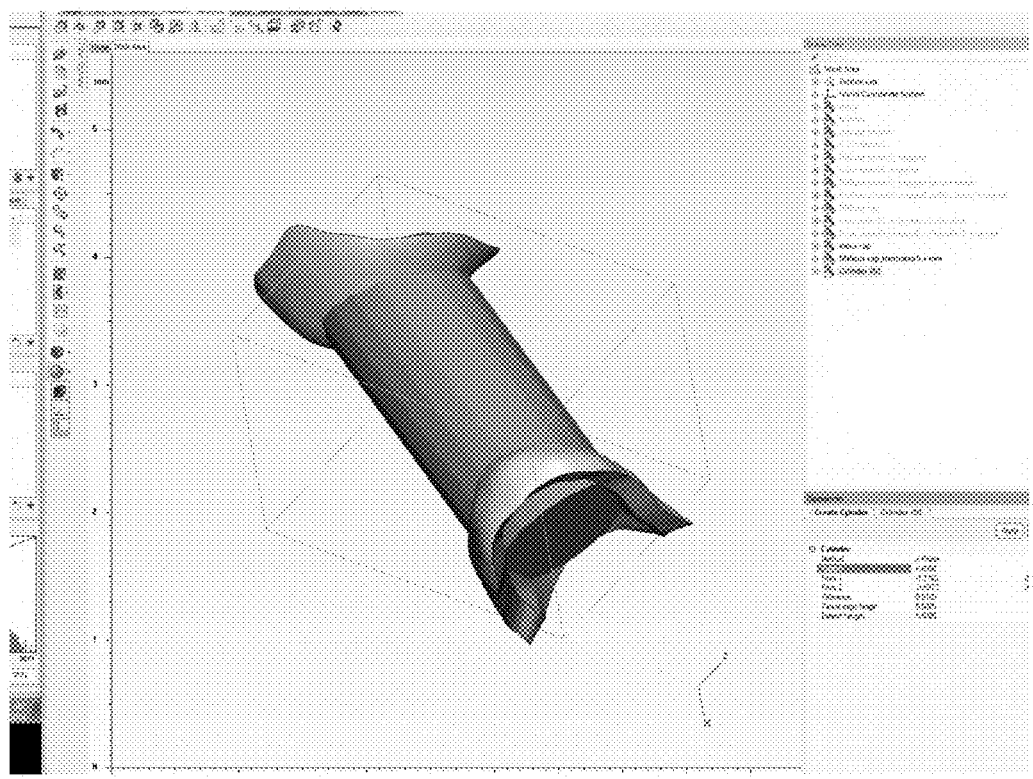
Figure 12P:
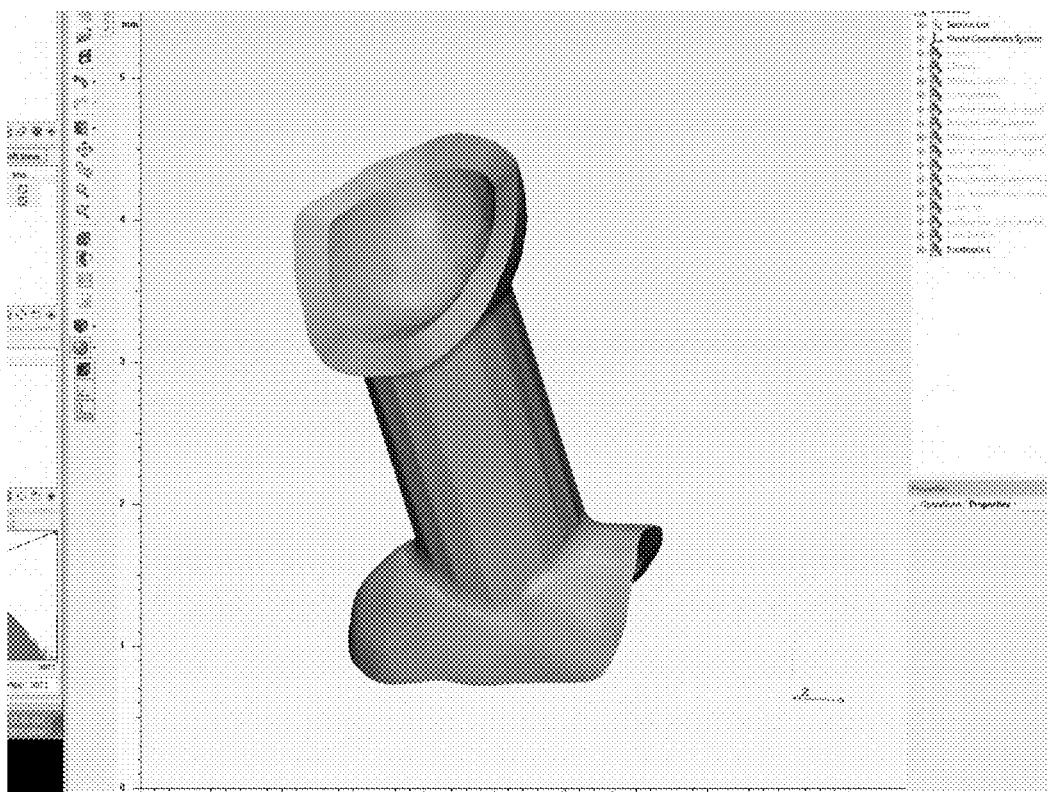
Figure 12Q:
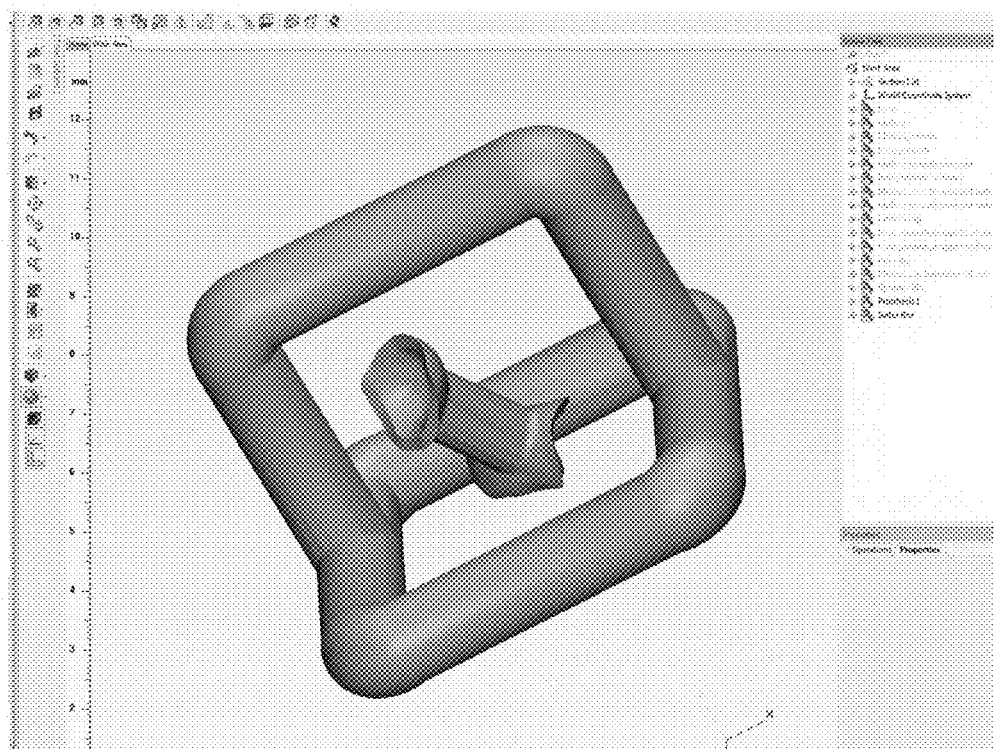
Figure 12R:
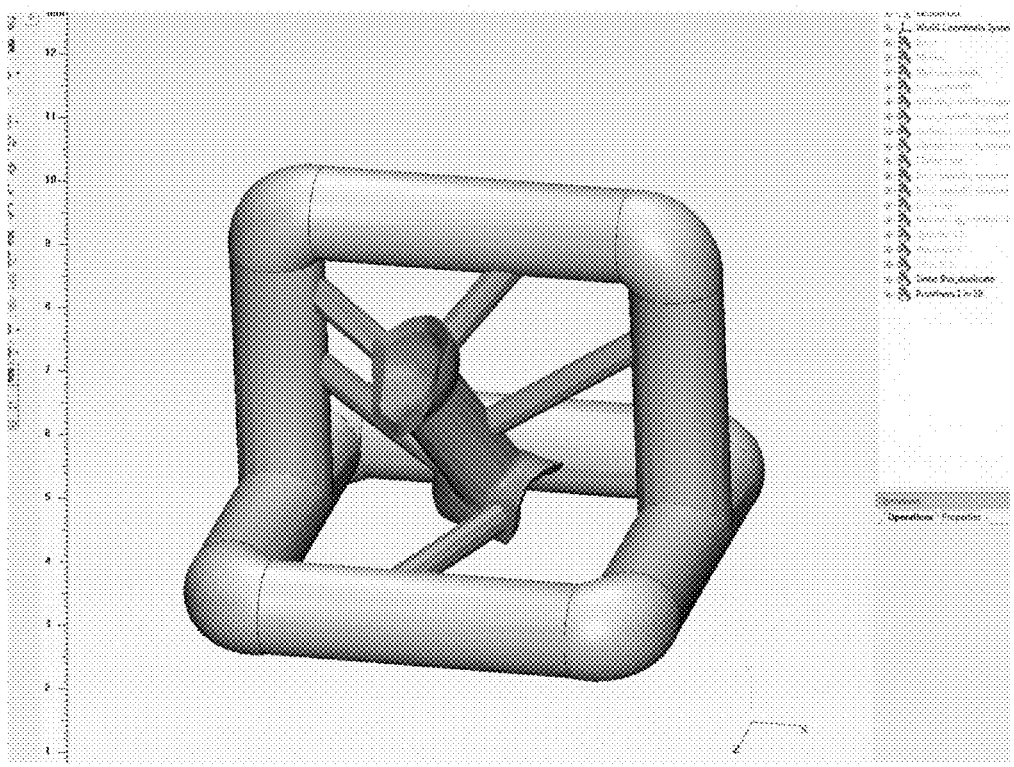
Figure 12S:
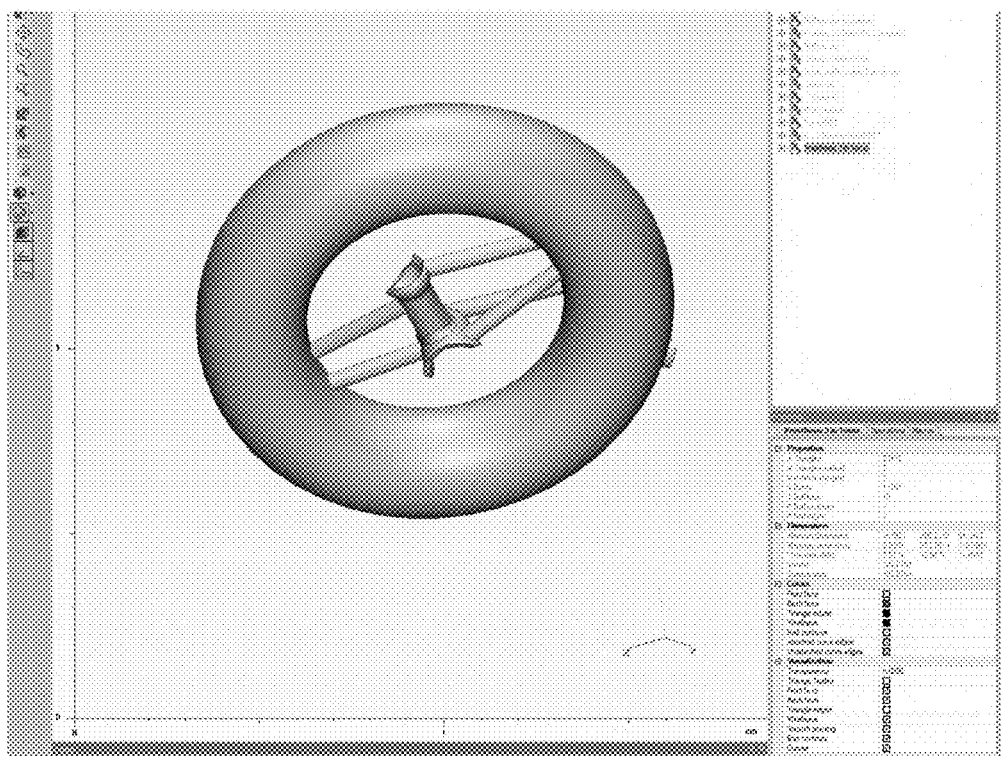
Figure 12T:
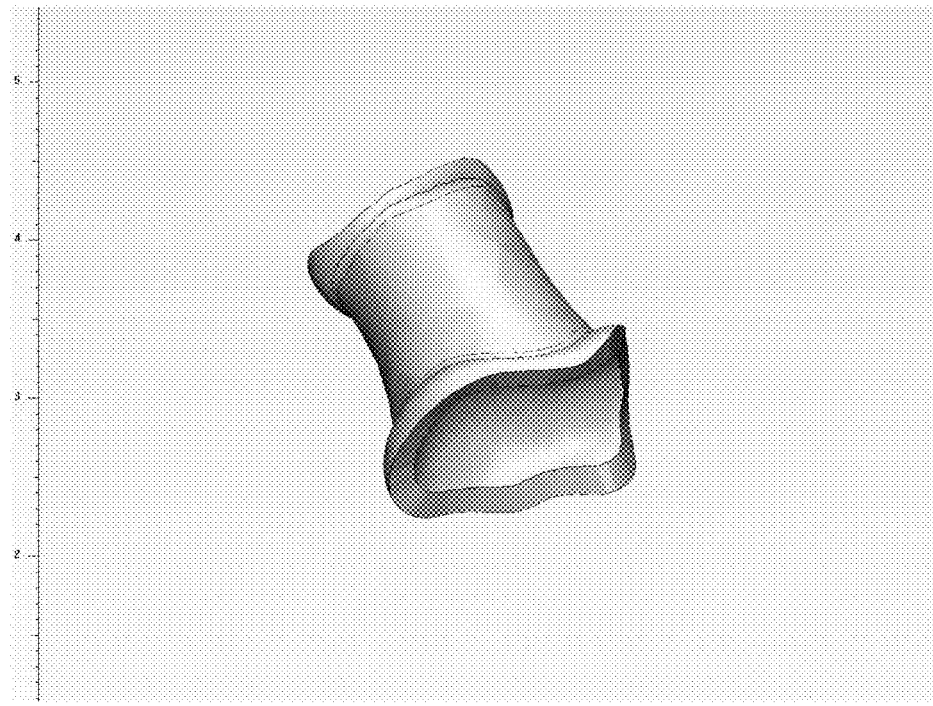
Figure 12U:
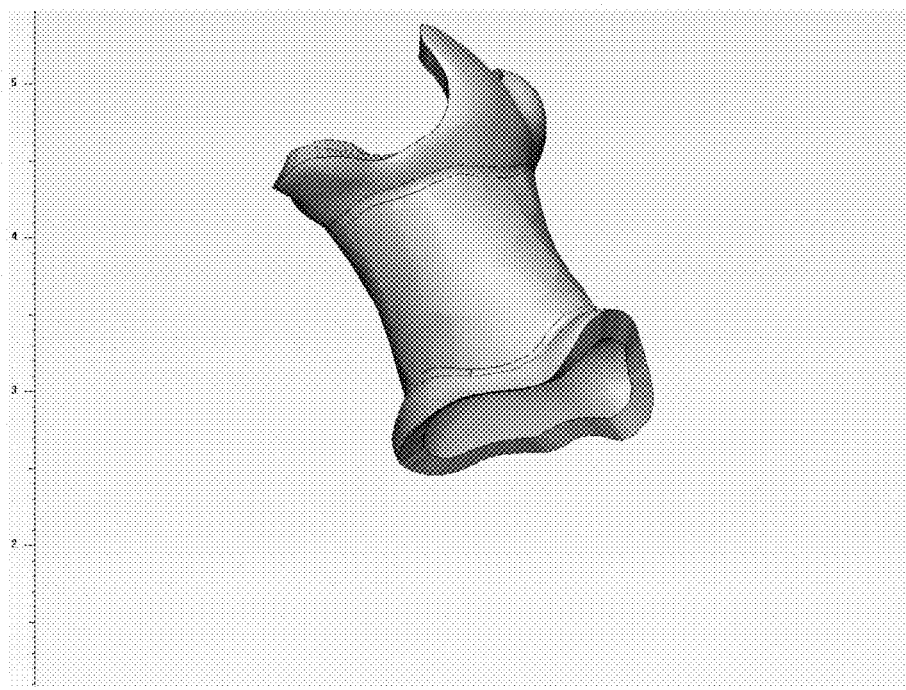
Figure 12V:
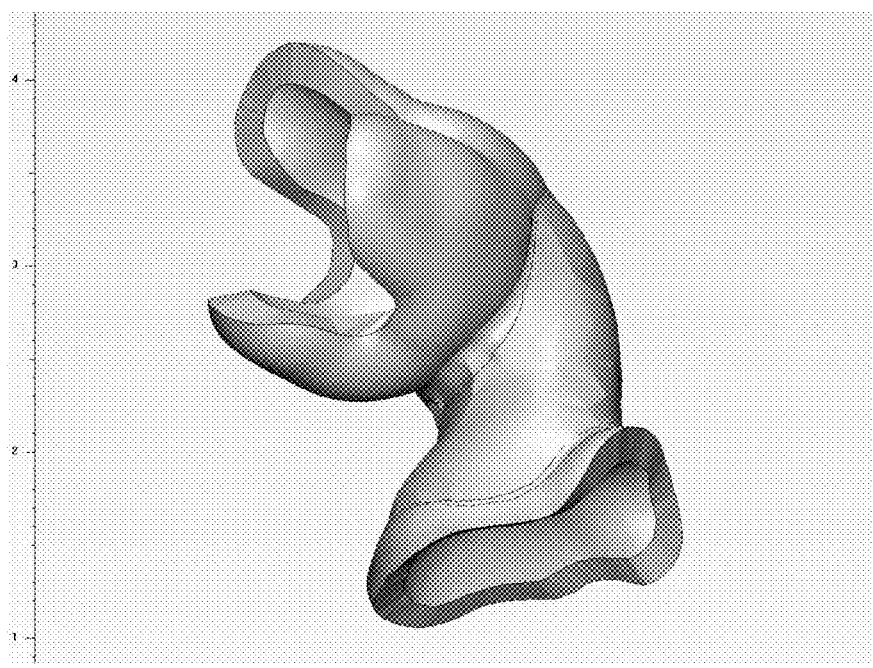
Figure 12W:
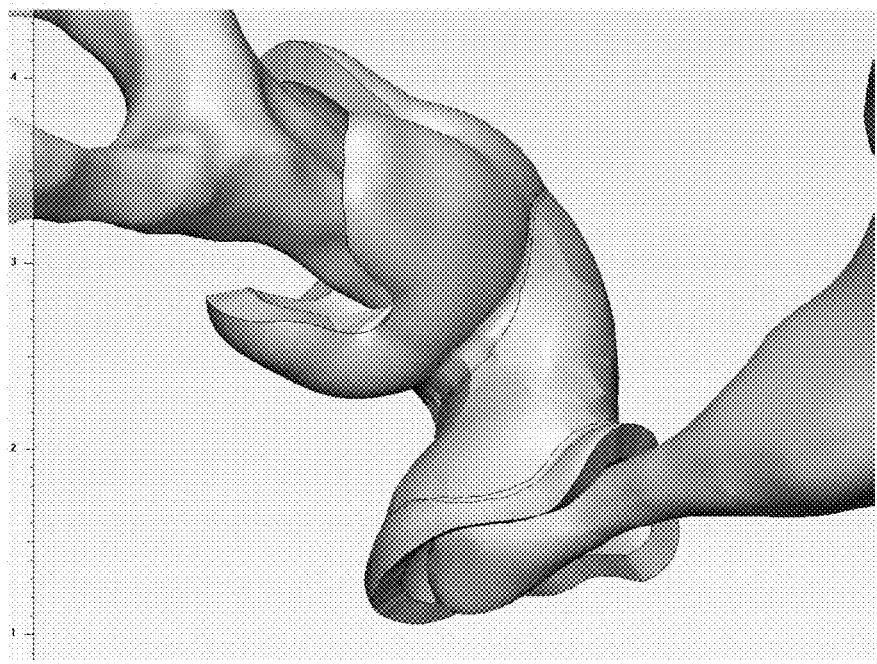
Figure 12X:
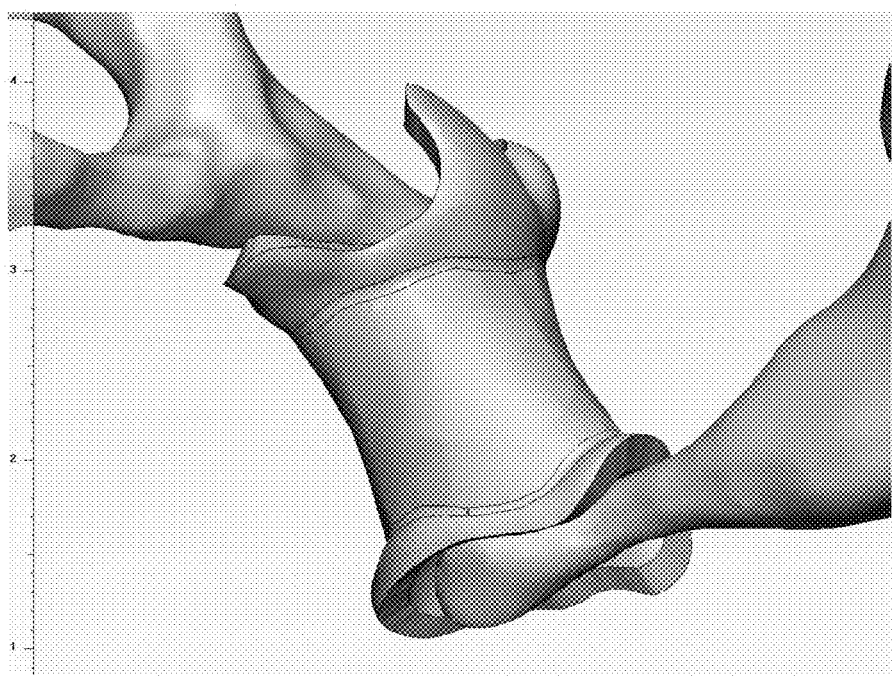
Figure 12Y:
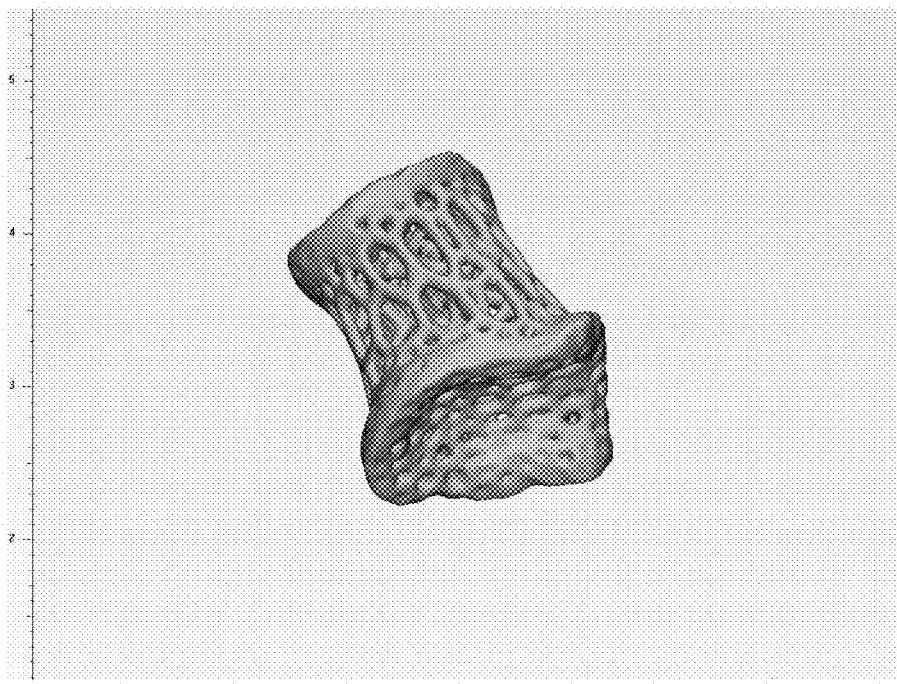

As mentioned above, processor 143 processes data from medical imaging machine 12 to generate a computer controlled manufacturing machine input file, which process is shown in greater detail in FIG. 11. At step 1100, processor 143 generates a 3D model of the patient's malleus 100 from data received from medical imaging machine 12. At step 1110, processor 143 generates a 3D model of the patient's stapes 120. Generation of the 3D model of the patient's stapes is particularly carried out by generating a 3D model of at least the head of the capitulum of the patient's stapes from the medical imaging machine 12, and causing the 3D modeling software to estimate the shape of at least a portion of the patient's stapes for that portion that is not described by the CT imaging data (e.g., because the CT scanning equipment is unable to discern the details of such portions of the patient's stapes). FIG. 12(*d*) shows a user interface screen generated by computer system 14 and depicting a first draft rendering of a patient's malleus 100 and stapes 120. Here, the 3D rendering of the malleus is accurate, as the malleus is a relatively large, densely ossified structure. The bone mask is thus able to capture the malleus very well, such that the 3D object creation from the mask then accurately represents the malleus. However, the 3D rendering of the patient's stapes is not highly accurate, as the head and neck of the stapes (i.e., the more dense portions of the stapes) are typically the only features capable of detection by medical imaging machine 12. The crus of the stapes are only faintly visible, and thus are manually added to the mask by an operator. While this results in a 3D model reflecting a somewhat misshapen stapes overall, the location and the shape of the head of the stapes is nonetheless highly accurate and is the only surface of the stapes used in forming the customized ossicular prostheses described herein. FIG. 12(*e*) shows a finished 3D model of the patient's malleus 100, where only minor adjustments are required to finish the malleus. The mesh that the 3D digital prosthesis design software uses to model the elements is subdivided twice to increase the number of triangles, which lessens the impact of the local smoothing tool and allows for a smoother curve to the surface. A smooth operation and wrap operation may be applied to finish the mesh. Likewise, FIG. 12(*f*) shows a finished 3D model of the patient's stapes 120. Here, the stapes mesh is subdivided to increase the number of triangles. The model is wrapped and smoothed, with local smoothing focused on the head of the stapes. The crus is crudely finished, as this portion of the stapes does not impact the prosthesis fabrication.

With reference to FIG. 12(*g*), the finished concave surfaces of the linear trough and incus cup need to be widened to accommodate the true bone/periosteum anatomy, which is likely underestimated with CT imaging. In order to widen the concave surfaces of the linear trough and incus cup, the mesh from both bones are wrapped with a 0.2 mm offset. The prosthesis will then use this new larger surface as a guide for fabrication.

Next and with reference to FIG. 12(*h*), the bone gap between the patient's malleus 100 and stapes 120 is aligned to select the location of the incus cup and linear trough. Here, the manubrium of the malleus is aligned over the head of the stapes by rotating the scene. The malleus is then hidden to expose the incus. A circular area around the epicenter of the incus is selected for creation of the cup. As shown in FIG. 12(*i*), the surface of the incus cup that is to be used for formation of cup 70 is selected, and a similar process is used to select the surface of the linear trough to be used for formation of linear trough 60 (see FIG. 12(*j*)). Preferably, and as shown in FIG. 12(*k*), each selected surface is wrapped with a 0.2 mm offset for fabrication of the cup 70 and trough 60, to provide the components with greater thickness.

With continuing reference to FIG. 11, at step 1120, processor 143 generates a 3D model of a linear trough 60 sized and configured to align with and fit over the manubrium of the patient's malleus. The 3D modeling software is used to size and configure the closed end of linear trough 60 to fit over the umbo at the distal end of the manubrium of the patient's malleus (see FIG. 5). As shown in FIG. 12(*l*), the linear trough 76 is created by subtracting the wrapped malleus from the wrapped malleus surface select. To finish the linear trough 50, the "chamfer edge" tool is used to remove the sharp margin with a setting of preferably 0.3 mm from each side of the edge. Next, processor 143 determines an inertial axis of rotation for linear trough 60, and defines a trough primary axis extending through the center of inertia of linear trough 60 and perpendicular to the concave face of the linear trough 60.

At step 1130, processor 143 generates a 3D model of a cup 70 to fit over the capitulum (head) of the patient's stapes. The 3D modeling software is used to size and configure the cup 70 to fit over the capitulum of the patient's stapes (see FIG. 5). As shown in FIG. 12(*m*), the cup 70 is formed with preferably a 0.2 mm chamfer. Next, processor 143 determines an inertial axis of rotation of the cup 70, and defines a cup primary axis extending through the center of inertia of the cup 70 and perpendicular to the concave face of the cup 70.

At step 1140, processor 143 generates a 3D model of a connecting strut extending between the cup 70 and the linear trough 60. The 3D modeling software is used to determine a linear distance between the center of inertia of the linear trough 60 and the center of inertia of cup 70, and to establish such distance as the length of the customized ossicular prosthetic. Next, processor 143 establishes a reference line extending between the center of inertia of linear trough 60 and the center of inertia of cup 70. Preferably, and as shown in FIG. 12(*n*), the distance between the cup 70 and the linear trough 60 is increased by 0.4 mm in order to compensate for length lost in oversizing the surfaces in FIG. 12(*g*), moving the trough 60 away from the cup 70 along the inertia axis. This may be accomplished using an "Interactive Translate" tool in the 3D modeling software. Processor 143 then defines an angular deviation between the primary axis of linear trough 60 and the reference line, defines an angular deviation between the primary axis of cup 70 and the reference line, and defines an angular rotation of trough 60 to cup 70 as discussed above. With reference to FIG. 12(*o*), the linear trough 60 and cup 70 may be attached with cylinder 80 used as a connecting post. For example, cylinder 80 may have a radius of 0.6 mm, and the total length of cylinder 80 is extended a distance of 0.5 mm to ensure that the edges of the cylinder are in contact with the convex surfaces of the linear trough 60 and the cup 70.

At step 1150, processor 134 generates a 3D model of a completed ossicular prosthesis 50 from the 3D model of the linear trough, the 3D model of the cup, and the 3D model of the connecting strut, with the positions of such elements being established as described above using the defined angular deviations and angular rotation. FIG. 12(*p*) reflects a display of the 3D model of the completed ossicular prosthesis, with post 80 connected to the linear trough 60 and cup 70. A local Boolean function may be used to combine post 80 to the convex surfaces of the trough 60 and cup 70. A fillet operation is used to smooth the margin between the post 80 and the trough 60 and cup 70.

Finally, at step 1160, processor 134 generates a 3D model of the completed ossicular prosthesis 50 within a sinter box 90 for ease of manufacturing the customized ossicular prosthesis 50 in computer controlled manufacturing machine 16, as shown in FIG. 12(*q*). More particularly, 3D printers may experience problems and printing errors when attempting to print small objects. In order to prevent this from occurring, a sinter box may be used, comprising a cage in which the small part can be nested. The combination of the sinter box and small part creates a larger part that is more recognizable to the printer software and less likely to cause an error. Moreover, as an additional benefit, the small parts may be maintained in the sinter box until they are used, because it helps keep track of the part and thus prevent its loss. After the sinter box is modeled, and as shown in FIG. 12(*r*), thin supports 92 are added to attach the prosthesis to the sinter box, which in an exemplary configuration may be 0.5 mm in diameter. Those skilled in the art will recognize that a sinter box 90 may take many shapes, such as (by way of non-limiting example) the form of a torus as shown in FIG. 12(*s*), which provides a continuous surface in which to attach support cylinders 92, which may ease fabrication. Other shapes and configurations of sinter box 90 may likewise be used without departing from the spirit and scope of the invention.

FIGS. 12(*t*)-12(*y*) show various screen displays generated by computer system 14 reflecting variations of 3D models of completed, customized ossicular prostheses that may be generated using the foregoing methods. More particularly, FIG. 12(*t*) shows the completed ossicular prosthesis with linear trough 60 and cup 70 configured as described above. FIG. 12(*u*) shows the completed ossicular prosthesis with linear trough 60 configured as described above, and cup 70 having prongs to provide enhanced gripping of the patient's stapes. FIG. 12(*v*) shows the completed ossicular prosthesis 50 configured so that the cup 70 is shifted to align more along the axis of the patient's stapes. In the exemplary configuration of FIG. 12(*v*), the cup 70 is also thicker with a 0.3 mm offset to make the prongs stronger and more likely to print. The connection of cup 70 to the trough 60 is curved in the configuration of FIG. 12(*v*) due to the change in position of the cup 70 with respect to the linear trough 60. FIG. 12(*w*) shows the prosthesis of FIG. 12(*v*) in position on axis with the patient's ossicles. Likewise, FIG. 12(*x*) shows the prosthesis of FIG. 12(*u*) in position on axis with the patient's ossicles. Finally, FIG. 12(*y*) shows an alternative configuration of the customized ossicular prosthesis having perforations that will provide a lattice for tissue ingrowth.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for generating an ossicular prosthesis that is customized to a patient's unique middle ear anatomy, comprising the steps of:
   receiving at a processor image data representing an anatomy of a patient's middle ear from a medical imaging machine;
   converting at said processor said image data representing an anatomy of a patient's middle ear into 3D model data representing an electronic 3D model of an ossicular prosthesis that is customized to a patient's unique middle ear anatomy;
   generating at said processor a data input file configured to instruct a computer controlled manufacturing machine to create a physical ossicular prosthesis conforming to said 3D model; and
   transmitting from said processor said data input file to a computer controlled manufacturing machine to cause said computer controlled manufacturing machine to generate said physical ossicular prosthesis.

2. The method of claim 1, wherein said step of converting said image data further comprises:
   generating 3D malleus model data representing an electronic 3D model of the patient's malleus; and
   generating 3D stapes model data representing an electronic 3D model of the head of the patient's stapes, and an electronic 3D model estimation of a remaining portion of the patient's stapes.

3. The method of claim 2, wherein the step of converting said image data further comprises:
   generating a 3D model of a linear trough sized and configured to align with and fit over a manubrium of the patient's malleus;
   generating a 3D model of a cup sized and configured to fit over the head of the patient's stapes; and
   generating a 3D model of a connecting strut extending between the linear trough and the cup.

4. The method of claim 3, wherein the step of converting said image data further comprises:
   generating a 3D model of a completed ossicular prosthesis attached to a sinter box.

5. The method of claim 2, wherein the step of generating 3D stapes model data further comprises generating a 3D model of at least the head of the capitulum of the patient's stapes, and causing the processor to estimate a shape of at least a portion of the patient's stapes that is not described by said image data.

6. The method of claim 2, further comprising the step of causing said processor to align a bone gap between the 3D model of the patient's malleus and the 3D model of the head of the patient's stapes.

7. The method of claim 6, wherein said step of aligning a bone gap further comprises causing said processor to align the manubrium of the 3D model of the patient's malleus over the 3D model of the head of the patient's stapes, the method further comprising the steps of:
   causing the processor to designate a circular area around an epicenter of the incus of the 3D model of the patient's stapes for creation of the cup; and
   causing the processor to designate an area along said 3D model of the patient's malleus for creation of the linear trough, wherein said area aligns along said bone gap with said circular area around an epicenter of the incus of the 3D model of the patient's stapes.

8. An ossicular prosthesis that is customized to a patient's unique middle ear anatomy formed by the method of claim 1.

9. A system for manufacturing an ossicular prosthesis that is customized to a patient's unique middle ear anatomy, comprising:
 a medical imaging machine;
 a computer system in data communication with said medical imaging machine; and
 a computer controlled manufacturing machine in data communication with said computer system;
 said computer system including a processor operably configured to:
  receive at said processor image data representing an anatomy of a patient's middle ear from said medical imaging machine;
  convert at said processor said image data representing an anatomy of a patient's middle ear into 3D model data representing an electronic 3D model of an ossicular prosthesis that is customized to a patient's unique middle ear anatomy;
  generate at said processor a data input file configured to instruct said computer controlled manufacturing machine to create a physical ossicular prosthesis conforming to said 3D model; and
  transmit from said processor said data input file to a computer controlled manufacturing machine to cause said computer controlled manufacturing machine to generate said physical ossicular prosthesis.

10. The system of claim 9, wherein said processor is further operably configured to convert said image data by:
 generating 3D malleus model data representing an electronic 3D model of the patient's malleus; and
 generating 3D stapes model data representing an electronic 3D model of the head of the patient's stapes, and an electronic 3D model estimation of a remaining portion of the patient's stapes.

11. The system of claim 10, wherein said processor is further operably configured to convert said image data by:
 generating a 3D model of a linear trough sized and configured to align with and fit over a manubrium of the patient's malleus;
 generating a 3D model of a cup sized and configured to fit over the head of the patient's stapes; and
 generating a 3D model of a connecting strut extending between the linear trough and the cup.

12. The system of claim 11, wherein said processor is further operably configured to convert said image by:
 generating a 3D model of a completed ossicular prosthesis attached to a sinter box.

13. The system of claim 10, wherein said processor is further operably configured to generate said 3D stapes model data by generating a 3D model of at least the head of the capitulum of the patient's stapes, and causing the processor to estimate a shape of at least a portion of the patient's stapes that is not described by said image data.

14. The system of claim 10, wherein said processor is further operably configured to align a bone gap between the 3D model of the patient's malleus and the 3D model of the head of the patient's stapes.

15. The system of claim 14, wherein said processor is further operably configured to align a bone gap by causing said processor to align the manubrium of the 3D model of the patient's malleus over the 3D model of the head of the patient's stapes, and is further operably configured to:
 designate a circular area around an epicenter of the incus of the 3D model of the patient's stapes for creation of the cup; and
 designate an area along said 3D model of the patient's malleus for creation of the linear trough, wherein said area aligns along said bone gap with said circular area around an epicenter of the incus of the 3D model of the patient's stapes.

* * * * *